(12) United States Patent
Kim et al.

(10) Patent No.: US 9,969,842 B2
(45) Date of Patent: May 15, 2018

(54) METHOD OF PREPARING POLY(ALKYLENE CARBONATE) VIA COPOLYMERIZATION OF CARBON DIOXIDE/EPOXIDE IN THE PRESENCE OF NOVEL COMPLEX

(71) Applicant: SK Innovation Co., Ltd., Seoul (KR)

(72) Inventors: Jong Chan Kim, Daejeon (KR); Han Sol Lee, Daejeon (KR); Hyo Seung Park, Daejeon (KR); Kwang Kuk Lee, Daejeon (KR); Jin Su Ham, Daejeon (KR); Jong Ho Lim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days. days.

(21) Appl. No.: 14/777,861

(22) PCT Filed: Mar. 20, 2014

(86) PCT No.: PCT/KR2014/002321
§ 371 (c)(1),
(2) Date: Sep. 17, 2015

(87) PCT Pub. No.: WO2014/148825
PCT Pub. Date: Sep. 25, 2014

(65) Prior Publication Data
US 2016/0304664 A1 Oct. 20, 2016

(30) Foreign Application Priority Data
Mar. 21, 2013 (KR) .................. 10-2013-0030179

(51) Int. Cl.
| | |
|---|---|
| C08G 64/34 | (2006.01) |
| C08G 64/02 | (2006.01) |
| C07F 11/00 | (2006.01) |
| C07F 15/06 | (2006.01) |
| C07F 15/00 | (2006.01) |

(52) U.S. Cl.
CPC .............. *C08G 64/34* (2013.01); *C07F 11/00* (2013.01); *C07F 15/00* (2013.01); *C07F 15/065* (2013.01); *C08G 64/0208* (2013.01)

(58) Field of Classification Search
CPC .................................................... C08G 64/34
USPC ........................................................ 528/405
See application file for complete search history.

(56) References Cited

U.S. PATENT DOCUMENTS

| | | | |
|---|---|---|---|
| 4,528,364 A | 7/1985 | Prier | |
| 4,686,276 A | 8/1987 | Myers | |
| 4,826,887 A | 5/1989 | Kuyper et al. | |
| 4,931,486 A | 6/1990 | Myers | |
| 5,066,762 A | 11/1991 | Ohbuchi et al. | |
| 5,070,173 A | 12/1991 | Yokota et al. | |
| 5,171,830 A | 12/1992 | Grey | |
| 5,847,069 A | 12/1998 | Greco | |
| 5,863,627 A | 1/1999 | Szycher et al. | |
| 6,197,051 B1 | 3/2001 | Zhong | |
| 8,247,520 B2 | 8/2012 | Allen et al. | |
| 8,530,616 B2 | 9/2013 | Jeong et al. | |
| 8,598,309 B2 | 12/2013 | Jeong et al. | |
| 8,987,411 B2 | 3/2015 | Jeong et al. | |
| 9,115,161 B2 | 8/2015 | Lee et al. | |
| 9,327,280 B2 | 5/2016 | Lee et al. | |
| 2010/0121026 A1 | 5/2010 | Lee et al. | |
| 2011/0230580 A1 | 9/2011 | Allen et al. | |
| 2011/0245424 A1 | 10/2011 | Jeong et al. | |
| 2015/0051369 A1 | 2/2015 | Allen et al. | |
| 2016/0304664 A1 | 10/2016 | Kim et al. | |

FOREIGN PATENT DOCUMENTS

| | | |
|---|---|---|
| CN | 1060299 A | 4/1992 |
| CN | 101020747 A | 8/2007 |
| CN | 101327452 A | 12/2008 |
| CN | 101687987 A | 3/2010 |
| CN | 102212085 A | 10/2011 |
| CN | 102939319 A | 2/2013 |
| EP | 0222453 B1 | 5/1987 |
| EP | 0302712 A2 | 2/1989 |
| EP | 0311278 A1 | 4/1989 |
| EP | 0798328 A2 | 10/1997 |
| KR | 100853358 B1 | 8/2008 |

(Continued)

OTHER PUBLICATIONS

Noh et al., "Two Components in a Molecule: Highly Efficient and Thermally Robust Catalytic System for CO2/Epoxide Copolymerization", J. Am. Chem. Soc., 2007, pp. 8082-8083, vol. 129.
Na et al., "Elucidation of the Structure of a Highly Active Catalytic System for CO2/Epoxide Copolymerization: A salen-Cobaltate Complex of an Unusual Binding Mode", Inorg. Chem., 2009, pp. 10455-10465, vol. 48.
Min et al., "Efficient Synthesis of a Highly Active Catalyst for CO2/Epoxide Copolymerization", Bull. Korean Chem. Soc., 2009, pp. 745-748; vol. 30, No. 3.
Kuran, "Poly(Propylene Carbonate)", Polymeric Materials Encyclopedia, J.C. Salamone, Ed., CRC Press, Inc., Boca Raton, 1996, pp. 6623-6630, vol. 9.
Cao et al., "Crosslinked polycarbonate polyurethanes: preparation and physical properties", Polymer, 1992, pp. 1384-1390, vol. 33, No. 7.
Gunatillake et al., "Synthesis and Characterization of a Series of Poly(alkylene carbonate) Macrodiols and the Effect of Their Structure on the Properties of Polyurethanes", Journal of Applied Polymer Science, 1998, pp. 1621-1633, vol. 69.

(Continued)

*Primary Examiner* — Duc Truong
(74) *Attorney, Agent, or Firm* — The Webb Law Firm

(57) ABSTRACT

Provided is a method of preparing poly(alkylene carbonate) using a molecular weight regulator in a process of preparing a copolymer of carbon dioxide/epoxide using a novel complex synthesized from salen-type ligand including a quaternary ammonium salt as a catalyst. According to the present invention, even though the molecular weight regulator is used, an activity of the catalyst may be stably maintained, whereby the low molecular weight of poly(alkylene carbonate) having a desirable level may be effectively provided. In addition, it is expected that since the novel complex as the catalyst of the present invention has a simple structure as compared to the existing copolymerization catalyst, due to the economical preparation cost thereof, the novel complex may be effectively applied to a large-scale commercial process.

9 Claims, No Drawings

(56) References Cited

FOREIGN PATENT DOCUMENTS

| KR | 20090090154 A | 8/2009 |
|---|---|---|
| KR | 20100067593 A | 6/2010 |
| KR | 20100136310 A | 12/2010 |
| KR | 20110097282 A | 8/2011 |
| KR | 20110112061 A | 10/2011 |
| WO | 9857671 A2 | 12/1998 |
| WO | 2008136591 A1 | 11/2008 |
| WO | 2012158573 A1 | 11/2012 |
| WO | 2013090276 A1 | 6/2013 |
| WO | 2014148825 A1 | 9/2014 |

OTHER PUBLICATIONS

Harris et al., "Structural Features of Poly(Alkylene Ether Carbonate) Diols and Intermediates Formed during Their Preparation", Journal of Applied Polymer Science, 1989; pp. 1491-1511, vol. 37.

Harris et al., "Polyurethane Elastomers Based on Molecular Weight Advanced Poly(ethylene Ether Carbonate) Diols. I. Comparison to Commercial Diols", Journal of Applied Polymer Science, 1990, pp. 487-507, vol. 41.

Sujith et al., "A Highly Active and Recyclable Catalyst System for $CO_2$/Propylene Oxide Copolymerization", Agnew Chem. Int. Ed., 2008, pp. 7306-7309, vol. 47.

Biannic et al.; "Efficient Cobalt-Catalyzed Oxidative Conversion of Lignin Models to Benzoquinones"; Organic Letters; May 16, 2013; pp. 2730-2733; vol. 15:11.

Lu et al.; "Cobalt catalysts for the coupling of $CO2$ and epoxides to provide polycarbonates and cyclic carbonates"; Chem. Soc. Rev.; 2012; pp. 1462-1484; vol. 41.

METHOD OF PREPARING POLY(ALKYLENE CARBONATE) VIA COPOLYMERIZATION OF CARBON DIOXIDE/EPOXIDE IN THE PRESENCE OF NOVEL COMPLEX

CROSS-REFERENCE TO RELATED APPLICATIONS

This application is the United States national phase of International Application No. PCT/KR2014/002321 filed Mar. 20, 2014, and claims priority to Korean Patent Application No. 10-2013-0030179 filed Mar. 21, 2013, the disclosures of which are hereby incorporated in their entirety by reference.

BACKGROUND OF THE INVENTION

Technical Field

The present invention relates to a method of preparing poly(alkylene carbonate) using a molecular weight regulator in a process of preparing a copolymer of carbon dioxide/epoxide using a novel complex synthesized from a salen-type ligand including a quaternary ammonium salt as a catalyst.

Background Art

Poly(alkylene carbonate) is an easily biodegradable polymer and is useful for packaging or coating materials. Methods of preparing poly(alkylene carbonate) from an epoxide compound and carbon dioxide is highly ecofriendly in that they use no phosgene which is harmful compound and adopt easily available and inexpensive carbon dioxide.

Since 1960's, many researchers have developed various types of catalysts to prepare poly(alkylene carbonate) from an epoxide compound and carbon dioxide. Recently, a catalyst having high activity and high selectivity and synthesized from a salen: ([H₂ salen=N,N'-bis(3,5dialkylsalicylidene)1,2ethylenediamine]-type ligand including a quaternary ammonium salt has been published [Korean Patent Registration No. 10-0853358 (Registration Date: Aug. 13, 2008); Korean Patent Application No. 10-2008-0015454 (Filing Date: Feb. 20, 2008); PCT/KR2008/002453 (Filing Date: Apr. 30, 2008); *J. Am. Chem. Soc.* 2007, 129, 80828083 (Jul. 4, 2007); *Angew. Chem. Int. Ed.* 2008, 47, 73067309 (Sep. 8, 2008)]. The catalyst disclosed in Korean Patent Registration No. 10-0853358 shows high activity and high selectivity, and may provide a copolymer having a large molecular weight and may be polymerized at a high temperature to be applicable to commercial processes. Furthermore, this catalyst is advantageous because a quaternary ammonium salt is contained in the ligand, and thus the catalyst may be easily separated from a copolymer resulting from copolymerization of carbon dioxide and epoxide, and reused.

Also, the inventor of Korean Patent Registration No. 10-0853358 have carefully examined a structure of a particular catalyst having higher activity and higher selectivity among the catalyst group disclosed in the above patent, and have proved that such a catalyst has a peculiar structure in which a nitrogen atom of the salen ligand is not coordinated to a metal but an oxygen atom thereof only is coordinated thereto, which was not known until now (see Structure 1 below, *Inorg. Chem.* 2009, 48, 1045510465).

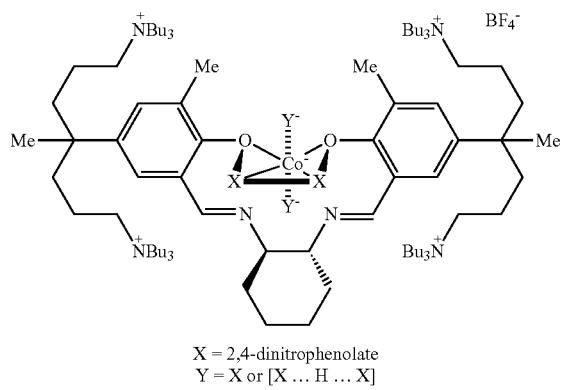

X = 2,4-dinitrophenolate
Y = X or [X ... H ... X]

Furthermore, a method of easily synthesizing the ligand of the compound of Structure 1 has been developed (*Bull. Korean Chem. Soc.* 2009, 30, 745748).

High molecular weight poly(alkylene carbonate) may be economically prepared using the compound of Structure 1 as a highly active catalyst. However, since poly(alkylene carbonate) has a low glass transition temperature (which is 40° C. in the case of poly(alkylene carbonate) prepared from propylene oxide and carbon dioxide) and has insufficient mechanical strength, predetermined limitations are imposed on the applications that may be developed therewith.

With the goal of overcoming the limitations of poly(alkylene carbonate), methods of preparing poly(alkylene carbonate)polyol having low molecular weight and a plurality of —OH terminal groups and preparing polyurethane therefrom have been developed. Polyurethane is a polymer obtained by reacting a compound having an —OH group with a compound having an isocyanate (—NCO) group thus forming a urethane bond (—NHC(O)O—). A variety of compounds having an —NCO group and compounds having an —OH group are being developed, and thermoplastic or thermosetting plastics or elastomeric polyurethanes having various physical properties have been developed and used. Polyurethane was prepared and used in an amount of about twelve million tons all over the world as of 2007, and the amount thereof is increased by 5% per year and the applications thereof have become wide. Examples of the compound having an OH group include diols and polyester diols having OH terminal groups, which have thousands of molecular weights obtained by ringopening polymerization of ethylene oxide or propylene oxide. Attempts have been made to prepare poly(alkylene carbonate)diol or polyol rather than poly(alkylene oxide)diol or polyester diol to thereby attain polyurethane (W. Kuran, Polymeric Materials Encyclopedia, J. C. Salamone, Ed. CRC Press, Inc., Boca Raton 1996, Vol. 9, p. 6623; *Polymer,* 1992, vol 33, 13841390). Polyurethane prepared from poly(alkylene carbonate)polyol is known to have higher hydrolyzability compared to urethane prepared from polyester polyol (EP 302712; U.S. Pat. No. 5,863,627), and is also reported to have greater antistatic effects (U.S. Pat. No. 4,931,486). Furthermore, thrombus coagulation resistance is reported to be high (WO 9857671).

EP 302712 (priority date: Aug. 4, 1987) and EP 311278 (priority date: Oct. 6, 1987) disclose polycarbonate diol prepared by condensing diethylcarbonate (EtOC(O)OEt) and 1,6hexanediol or 1,5petandediol, and preparation of polyurethane using the same. In addition, U.S. Pat. No.

5,171,830 (filing date: Aug. 16, 1991) discloses a method of synthesizing poly(alkylene carbonate) by condensing dialkyl carbonate (ROC(O)OR) and alpha, omegaalkanediol having 4 or more carbons in the presence of a base catalyst and preparation of a urethane resin using the same.

EP 798328A2 (priority date: Mar. 28, 1996) discloses synthesis of polycarbonatecopolyether diol using condensation of polyether diol and dimethylcarbonate (MeOC(O)OMe).

Also, synthesis of poly(alkylene carbonate)macrodiol using condensation of various diols and ethylene carbonate and preparation of polyurethane using the same are disclosed in *Journal of Applied Polymer Science*, 1998, 69, 16211633 and *Journal of Applied Polymer Science*, 1989, 37, 14911511.

However, such poly(alkylene carbonate)polyol is not prepared using copolymerization of carbon dioxide and epoxide and also has a different structure from that of a copolymer of carbon dioxide and epoxide. Specifically, in order to prepare poly(alkylene carbonate) using polycondensation of ethylene carbonate or dialkyl carbonate, diol having spaced 3 or more carbons should be used. That is, poly(alkylene carbonate) has a structure in which a carbonate bond is linked by 3 or more carbons. Poly(alkylene carbonate) prepared by copolymerization of carbon dioxide and epoxide has a structure in which a carbonate bond is linked by 2 carbons.

U.S. Pat. No. 4,686,276 (filing date: Dec. 30, 1985) discloses a method of synthesizing poly(ethylene carbonate) diol by copolymerizing carbon dioxide and ethylene oxide in the presence or absence of ethylene carbonate using a diol compound as an initiator and a catalyst consisting of an alkaline compound and a tin compound. In addition, U.S. Pat. No. 4,528,364 (filing date: Apr. 19, 1984) discloses a method of removing a catalyst from the prepared polymer compound. Here, the prepared polymer has carbon dioxide content less than 30%, which is not a complete alternating copolymer. In addition, preparation of polyurethane using poly(ethylene carbonate)diol which was prepared and purified by the above method is disclosed in *Journal of Applied Polymer Science*, 1990, 41, 487507.

EP 0222453 (filing date: Jun. 11, 1986) discloses a method of synthesizing polyol by copolymerizing carbon dioxide and epoxide using a double metal cyanide compound as a catalyst and using an organic material having reactive hydrogen as a molecular weight regulator. However, the obtained polyol has a carbon dioxide content of 5 to 13 mol %, which is not a pure poly(alkylene carbonate) compound based on complete alternating copolymerization of carbon dioxide and epoxide.

CN Patent No. 1060299A (filing date: Sep. 19, 1991), which is published later, discloses a method of preparing polyol by copolymerizing carbon dioxide and epoxide using a polymer supported bimetallic catalyst and using an organic material having 1 to 10 reactive hydrogen as a molecular weight regulator. However, the polyol prepared by Examples has a carbon dioxide content of 37 to 40 mol %, which is not a pure poly(alkylene carbonate) compound based on complete alternating copolymerization of carbon dioxide and epoxide.

U.S. Pat. No. 8,247,520 (filing date: Sep. 8, 2009) discloses a method of copolymerizing carbon dioxide and epoxide using a chain transfer agent which is a molecular weight regulator under a binary catalyst system of (salen)Co complex. However, the present inventors found that as an amount of the used chain transfer agent becomes increased in the copolymerization system, catalyst system activity is deteriorated, such that there is a limitation in obtaining low molecular weight of copolymer having desirable level.

As described above, synthesis of low molecular weight of poly(alkylene carbonate) by copolymerization of carbon dioxide/epoxide in the presence of a molecular weight regulator has been abundantly reported. Meanwhile, in order to prepare appropriate poly(alkylene carbonate) having low molecular weight in a large-scale commercial process, since maintenance of catalyst system activity in the preparation process as well as economical cost of copolymerization catalyst system are important, development of a novel catalyst system capable of satisfying the requirements has been demanded.

SUMMARY OF THE INVENTION

Technical Problem

An object of the present invention is to provide a method of preparing low molecular weight of poly(alkylene carbonate) using a molecular weight regulator in a process of preparing a copolymer of carbon dioxide and epoxide using a novel complex synthesized from salen-type ligand including a quaternary ammonium salt as a catalyst.

Another object of the present invention is to provide a method in which an activity of the catalyst is effectively maintained in the preparation process by using the novel complex as the copolymerization catalyst in the process of preparing the low molecular weight of poly(alkylene carbonate).

Solution to Problem

In one general aspect, a method of preparing poly(alkylene carbonate) comprises:

copolymerizing carbon dioxide and one or more epoxide compounds selected from a group consisting of (C2-C20) alkylene oxide substituted or unsubstituted with halogen, (C1-C20)alkyloxy, (C6-C20)aryloxy or (C6-C20)ar(C1-C20)alkyl(aralkyl)oxy; (C4-C20)cycloalkylene oxide substituted or unsubstituted with halogen, (C1-C20)alkyloxy, (C6-C20)aryloxy or (C6-C20)ar(C1-C20)alkyl(aralkyl)oxy; and (C8-C20)styrene oxide substituted or unsubstituted with halogen, (C1-C20)alkyloxy, (C6-C20)aryloxy, (C6-C20)ar (C1-C20)alkyl(aralkyl)oxy or (C1-C20)alkyl in the presence of the following compound represented by Chemical Formula 9 which is a molecular weight regulator, using the following complex represented by Chemical Formula 1 as a catalyst.

[Chemical Formula 1]

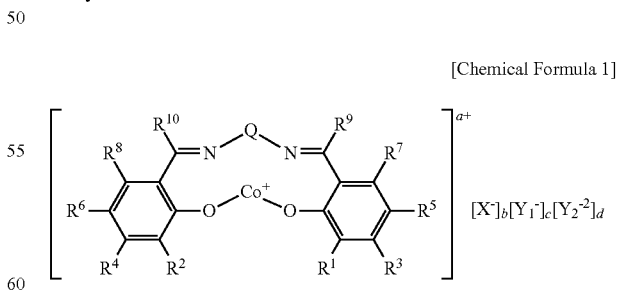

[In Chemical Formula 1,
M is trivalent cobalt or trivalent chromium;
A is an oxygen or sulfur atom;
Q is a diradical that connects two nitrogen atoms;
$R^1$ to $R^{10}$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; a metalloid radical of Group 14 metal substituted with hydrocarbyl; a protonated group of the following Chemical Formula 2; a protonated group of the following Chemical Formula 3; a protonated group of the following Chemical Formula 4; a protonated group of the following Chemical Formula 5; a protonated group of the following Chemical Formula 6; or a protonated group of the following Chemical Formula 7; two of $R^1$ to $R^{10}$ may be linked with each other by a protonated group of the following Chemical Formula 8 to thereby form a ring;

wherein at least two or more of $R^1$ to $R^{10}$ are a protonated group selected from a group consisting of the following Chemical Formulas 2, 3, 4, 5, 6 and 7; or two of $R^1$ to $R^{10}$ are linked with each other by a protonated group of the following Chemical Formula 8 to thereby form a ring;

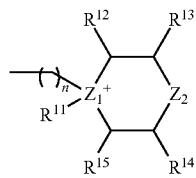
[Chemical Formula 2]

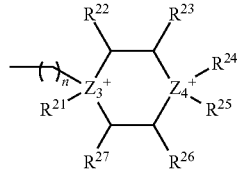
[Chemical Formula 3]

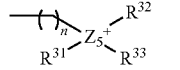
[Chemical Formula 4]

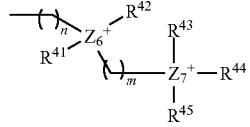
[Chemical Formula 5]

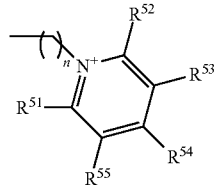
[Chemical Formula 6]

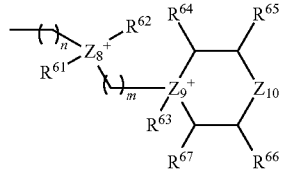
[Chemical Formula 7]

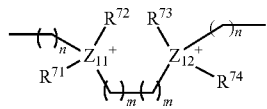
[Chemical Formula 8]

X— is a halogen anion; a (C6-C20)aryloxy anion; a (C6-C20)aryloxy anion containing one or more selected from among a halogen atom, a nitrogen atom, an oxygen atom, a silicon atom, a sulfur atom and a phosphorus atom; a (C1-C20)alkylcarboxyl anion; a (C1-C20)alkylcarboxyl anion containing one or more selected from among a halogen atom, a nitrogen atom, an oxygen atom, a silicon atom, a sulfur atom and a phosphorus atom; a (C6-C20)arylcarboxyl anion; a (C6-C20)arylcarboxyl anion containing one or more selected from among a halogen atom, a nitrogen atom, an oxygen atom, a silicon atom, a sulfur atom and a phosphorus atom; a (C1-C20)alkoxy anion; a (C1-C20)alkoxy anion containing one or more selected from among a halogen atom, a nitrogen atom, an oxygen atom, a silicon atom, a sulfur atom and a phosphorus atom; a (C1-C20)alkylcarbonate anion; a (C1-C20)alkylcarbonate anion containing one or more selected from among a halogen atom, a nitrogen atom, an oxygen atom, a silicon atom, a sulfur atom and a phosphorus atom; a (C6-C20)arylcarbonate anion; a (C6-C20)arylcarbonate anion containing one or more selected from among a halogen atom, a nitrogen atom, an oxygen atom, a silicon atom, a sulfur atom and a phosphorus atom; a (C1-C20)alkylsulfonate anion; a (C1-C20)alkylsulfonate anion containing one or more selected from among a halogen atom, a nitrogen atom, an oxygen atom, a silicon atom, a sulfur atom and a phosphorus atom; a (C1-C20)alkylamido anion; a (C1-C20)alkylamido anion containing one or more selected from among a halogen atom, a nitrogen atom, an oxygen atom, a silicon atom, a sulfur atom and a phosphorus atom; a (C6-C20)arylamido anion; a (C6-C20)arylamido anion containing one or more selected from among a halogen atom, a nitrogen atom, an oxygen atom, a silicon atom, a sulfur atom and a phosphorus atom; a (C1-C20)alkylcarbamate anion; a (C1-C20)alkylcarbamate anion containing one or more selected from among a halogen atom, a nitrogen atom, an oxygen atom, a silicon atom, a sulfur atom and a phosphorus atom; a (C6-C20)arylcarbamate anion; or a (C6-C20)arylcarbamate anion containing one or more selected from among a halogen atom, a nitrogen atom, an oxygen atom, a silicon atom, a sulfur atom and a phosphorus atom;

X— may be coordinated to M;

$Y_1^-$ is $F^-$, $Cl^-$, $Br^-$, $I^-$, $BF_4^-$, $ClO_4^-$, $NO_3^-$ or $PF_6^-$;

$Y_2^{-2}$ is $SO_4^{-2}$ or $CO_3^{-2}$;

a is an integer obtained by adding 1 to the total number of monovalent cations included in protonated groups of $R^1$ to $R^{10}$;

b is an integer of 1 or more, c is an integer of 0 or more, d is an integer of 0 or more, and b+c+2d=a is satisfied;

$Z_1$, $Z_3$, $Z_4$, $Z_5$, $Z_6$, $Z_7$, $Z_8$, $Z_9$, $Z_{11}$ and $Z_{12}$ are each independently an nitrogen atom or a phosphorus atom;

$Z_2$ and $Z_{10}$ are each independently an oxygen atom, a sulfur atom or a methylene group (—$CH_2$—);

n is an integer of 1 to 10, preferably 1 to 5;

m is an integer of 1 to 10, preferably 1 to 5;

$R^{11}$, $R^{12}$, $R^{13}$, $R^{14}$, $R^{15}$, $R^{21}$, $R^{22}$, $R^{23}$, $R^{24}$, $R^{25}$, $R^{26}$, $R^{27}$, $R^{41}$, $R^{42}$, $R^{43}$, $R^{44}$, $R^{45}$, $R^{51}$, $R^{52}$, $R^{53}$, $R^{54}$, $R^{55}$, $R^{61}$, $R^{62}$, $R^{63}$, $R^{64}$, $R^{65}$, $R^{66}$, $R^{67}$, $R^{71}$, $R^{72}$, $R^{73}$ and $R^{74}$ are each independently hydrogen; (C1-C20)alkyl; (C1-C20)alkyl containing one or more selected from among halogen, nitrogen, oxygen, silicon, sulfur and phosphorus; (C2-C20) alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl (C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; or a metalloid radical of Group 14 metal substituted with hydrocarbyl; two of $R^{11}$, $R^{12}$, $R^{13}$, $R^{14}$ and $R^{15}$, two of $R^{21}$, $R^{23}$, $R^{24}$, $R^{25}$, $R^{26}$ and $R^{27}$, two of $R^{41}$, $R^{42}$, $R^{43}$, $R^{44}$ and $R^{45}$, two of $R^{51}$, $R^{52}$, $R^{53}$, $R^{54}$ and $R^{55}$, two of $R^{61}$, $R^{62}$, $R^{63}$, $R^{64}$, $R^{65}$, $R^{66}$ and $R^{67}$ or two of $R^{71}$, $R^{72}$, $R^{73}$ and $R^{74}$ may be linked with each other to thereby form a ring; and $R^{31}$, $R^{32}$ and $R^{33}$ are each independently (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl (C1-C20)alkyl containing one or more selected from among halogen, nitrogen, oxygen, silicon, sulfur and phosphorus; or a metalloid radical of Group 14 metal substituted with hydrocarbyl; two of $R^{31}$, $R^{32}$ and $R^{33}$ may be linked with each other to thereby form a ring.]

$$J(LH)_c \quad \text{[Chemical Formula 9]}$$

[In Chemical Formula 9, J is C1 to C60 hydrocarbyl c-valent radical with or without an ether group, an ester group or an amine group; LH is —OH or —CO$_2$H; and c is an integer from 1 to 10, in which LH may be identical or different when c is 2 or more.]

Since the complex represented by Chemical Formula 1 structurally includes at least 2 or more onium salts in a molecule, the complex used as a catalyst has excellent activity and promotes polymerization even at a relatively low temperature. In addition, the complex represented by Chemical Formula 1 includes the form in which one or two or more onium salts symmetrically present at both sides based on a central metal, respectively, such that preparation yield of the complex may be improved.

Preferably, in the complex represented by Chemical Formula 1, Q may be (C6~C30)arylene, (C1~C20)alkylene, (C2~C20)alkenylene, (C2~C20)alkynylene or (C3~C20)cycloalkylene, more preferably, 1,2-cyclohexylene, phenylene or ethylene, and most preferably, trans-1,2-cyclohexylene.

Preferably, in the complex represented by Chemical Formula 1, M may be trivalent cobalt, and A may be oxygen.

Preferably, in the complex represented by Chemical Formula 1, $R^1$ to $R^{10}$ may be each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20) alkenyl containing one or more selected from among halogen, nitrogen, oxygen, silicon, sulfur and phosphorus; (C1-C20)alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20)alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20) arylcarbonyl; a metalloid radical of Group 14 metal substituted with hydrocarbyl; a protonated group of the following Chemical Formula 2; a protonated group of the following Chemical Formula 3; a protonated group of the following Chemical Formula 4; a protonated group of the following Chemical Formula 5; a protonated group of the following Chemical Formula 6; or a protonated group of the following Chemical Formula 7; two of $R^1$ to $R^{10}$ may be linked with each other by a protonated group of the following Chemical Formula 8 to thereby form a ring; wherein at least two or more of $R^1$, $R^2$, $R^5$ and $R^6$ are a protonated group selected from a group consisting of the following Chemical Formulas 2, 3, 4, 5, 6 and 7; or two of $R^1$, $R^2$, $R^5$ and $R^6$ are linked with each other by a protonated group of the following Chemical Formula 8 to thereby form a ring.

More preferably, in the complex represented by Chemical Formula 1, $R^3$, $R^4$, $R^7$, $R^8$, $R^9$ and $R^{10}$ are each hydrogen, $R^1$, $R^2$, $R^5$ and $R^6$ are each independently hydrogen; halogen; (C1-C20)alkyl; (C1-C20)alkyl containing one or more selected from among halogen, nitrogen, oxygen, silicon, sulfur and phosphorus; (C2-C20)alkenyl; (C2-C20)alkenyl containing one or more selected from among halogen, nitrogen, oxygen, silicon, sulfur and phosphorus; (C1-C20) alkyl(C6-C20)aryl; (C1-C20)alkyl(C6-C20)aryl containing one or more selected from among halogen, nitrogen, oxygen, silicon, sulfur and phosphorus; (C6-C20)aryl(C1-C20) alkyl; (C6-C20)aryl(C1-C20)alkyl containing one or more selected from among halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; a metalloid radical of Group 14 metal substituted with hydrocarbyl; a protonated group of the following Chemical Formula 2; a protonated group of the following Chemical Formula 3; a protonated group of the following Chemical Formula 4; a protonated group of the following Chemical Formula 5; a protonated group of the following Chemical Formula 6; or a protonated group of the following Chemical Formula 7; two of $R^1$, $R^2$, $R^5$ and $R^6$ may be linked with each other by a protonated group of the following Chemical Formula 8 to thereby form a ring; wherein at least two or more of $R^1$, $R^2$, $R^5$ and $R^6$ are a protonated group selected from a group consisting of Chemical Formulas 2, 3, 4, 5, 6 and 7; or two of $R^1$, $R^2$, $R^5$ and $R^6$ are linked with each other by a protonated group of Chemical Formula 8 to thereby form a ring.

More preferably, the present invention provides a method of preparing poly(alkylene carbonate), comprising:

copolymerizing carbon dioxide and one or more epoxide compounds selected from a group consisting of (C2-C20) alkylene oxide substituted or unsubstituted with halogen, (C1-C20)alkyloxy, (C6-C20)aryloxy or (C6-C20)ar(C1-C20)alkyl(aralkyl)oxy; (C4-C20)cycloalkylene oxide substituted or unsubstituted with halogen, (C1-C20)alkyloxy, (C6-C20)aryloxy or (C6-C20)ar(C1-C20)alkyl(aralkyl)oxy; and (C8-C20)styrene oxide substituted or unsubstituted with halogen, (C1-C20)alkyloxy, (C6-C20)aryloxy, (C6-C20)ar (C1-C20)alkyl(aralkyl)oxy or (C1-C20)alkyl in the presence of the compound represented by Chemical Formula 9 using a complex having the following structure represented by Chemical Formula 10 or 11 as a catalyst.

[Chemical Formula 10]

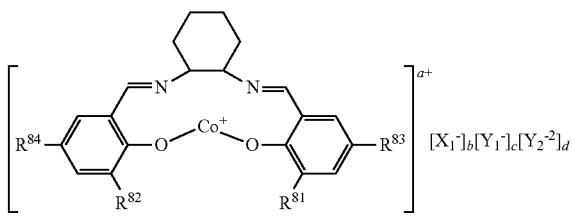

[In Chemical Formula 10, $R^{81}$ and $R^{82}$ identically represent methyl, ethyl, isopropyl, or tert-butyl; or a protonated group identically selected from a group consisting of Chemical Formula 2, Chemical Formula 3, Chemical Formula 4, Chemical Formula 5, Chemical Formula 6 and Chemical Formula 7;

$R^{83}$ and $R^{84}$ identically represent methyl, ethyl, isopropyl, or tert-butyl; or a protonated group identically selected from a group consisting of Chemical Formula 2, Chemical Formula 3, Chemical Formula 4, Chemical Formula 5, Chemical Formula 6 and Chemical Formula 7;

with the proviso that a case where $R^{81}$ and $R^{82}$ identically represent methyl, ethyl, isopropyl, or tert-butyl; and simultaneously $R^{83}$ and $R^{84}$ identically represent methyl, ethyl, isopropyl, or tert-butyl is excluded;

$X_1$— is a halogen anion; a (C1-C20)alkylcarboxyl anion; a (C1-C20)alkylcarboxyl anion containing one or more selected from among a halogen atom, a nitrogen atom, an oxygen atom, a silicon atom, a sulfur atom and a phosphorus atom; a (C1-C20)alkylcarbonate anion; a (C1-C20)alkylcarbonate anion containing one or more selected from among a halogen atom, a nitrogen atom, an oxygen atom, a silicon atom, a sulfur atom and a phosphorus atom; a (C1-C20) alkylcarbamate anion; or a (C1-C20)alkylcarbamate anion containing one or more selected from among a halogen atom, a nitrogen atom, an oxygen atom, a silicon atom, a sulfur atom and a phosphorus atom;

$X_1$— may be coordinated to Co;

$Y_1^-$ is $Cl^-$, $Br^-$, $BF_4^-$ or $NO_3^-$;

$Y_2^{-2}$ is $SO_4^{-2}$;

a is an integer obtained by adding 1 to the total number of monovalent cations included in protonated groups of $R^{81}$ to $R^{84}$; and b is an integer of 1 or more, c is an integer of 0 or more, d is an integer of 0 or more, and b+c+2d=a is satisfied.]

with the proviso that a case where $R^{85}$ and $R^{86}$ identically represent methyl, ethyl, isopropyl, or tert-butyl; and simultaneously $R^{87}$ and $R^{88}$ identically represent methyl, ethyl, isopropyl, or tert-butyl is excluded;

$X_2$— is a halogen anion; a (C1-C20)alkylcarboxyl anion; a (C1-C20)alkylcarboxyl anion containing one or more selected from among a halogen atom, a nitrogen atom, an oxygen atom, a silicon atom, a sulfur atom and a phosphorus atom; a (C1-C20)alkylcarbonate anion; a (C1-C20)alkylcarbonate anion containing one or more selected from among a halogen atom, a nitrogen atom, an oxygen atom, a silicon atom, a sulfur atom and a phosphorus atom; a (C1-C20) alkylcarbamate anion; or a (C1-C20)alkylcarbamate anion containing one or more selected from among a halogen atom, a nitrogen atom, an oxygen atom, a silicon atom, a sulfur atom and a phosphorus atom;

$X_2$— may be coordinated to Co;

$Y_3^-$ is $Cl^-$, $Br^-$, $BF_4^-$ or $NO_3^-$;

$Y_4^{-2}$ is $SO_4^{-2}$;

e is an integer obtained by adding 1 to the total number of monovalent cations included in protonated groups of $R^{85}$ to $R^{88}$; and f is an integer of 1 or more, g is an integer of 0 or more, h is an integer of 0 or more, and f+g+2h=e is satisfied.]

Most preferably, the present invention provides a method of preparing poly(alkylene carbonate), comprising:

copolymerizing carbon dioxide and one or more epoxide compounds selected from a group consisting of (C2-C20) alkylene oxide substituted or unsubstituted with halogen, (C1-C20)alkyloxy, (C6-C20)aryloxy or (C6-C20)ar(C1-C20)alkyl(aralkyl)oxy; (C4-C20)cycloalkylene oxide substituted or unsubstituted with halogen, (C1-C20)alkyloxy, (C6-C20)aryloxy or (C6-C20)ar(C1-C20)alkyl(aralkyl)oxy; and (C8-C20)styrene oxide substituted or unsubstituted with halogen, (C1-C20)alkyloxy, (C6-C20)aryloxy, (C6-C20)ar (C1-C20)alkyl(aralkyl)oxy or (C1-C20)alkyl in the presence of the compound represented by Chemical Formula 9 using a complex having a structure represented by one of the following Chemical Formulas 12 to 21 as a catalyst.

Since the complex having a structure represented by one of the following Chemical Formulas 12 to 21 includes one or two onium salt(s) symmetrically present at both sides based on a central metal (two or four onium salts are entirely present in the molecule of the complex), respectively, preparation yield of the complex may be more improved, which is the most preferred.

[Chemical Formula 11]

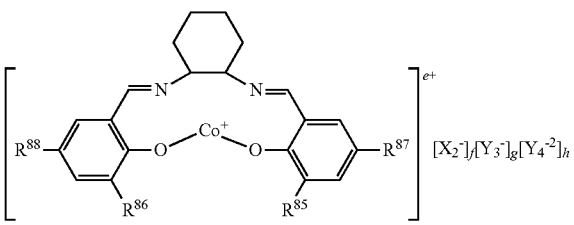

[In Chemical Formula 11, $R^{85}$ and $R^{86}$ identically represent methyl, ethyl, isopropyl, or tert-butyl; or are linked with each other by a protonated group of Chemical Formula 8 to thereby form a ring;

$R^{87}$ and $R^{88}$ identically represent methyl, ethyl, isopropyl, or tert-butyl; or are linked with each other by a protonated group of Chemical Formula 8 to thereby form a ring;

[Chemical Formula 12]

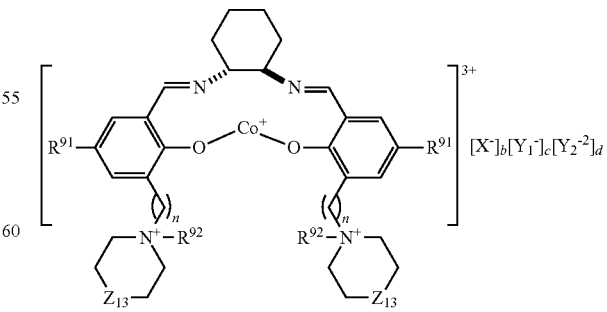

[In Chemical Formula 12, $R^{91}$ is methyl, ethyl, isopropyl or tert-butyl;

$R^{92}$ is (C1-C20)alkyl;

$Z_{13}$ is an oxygen atom, a sulfur atom or a methylene group (—$CH_2$—);

n is an integer of 1 to 10, preferably 1 to 5;

X— is Cl— or an acetate anion ($CH_3COO$—);

X— may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=3 is satisfied.]

n is an integer of 1 to 10, preferably 1 to 5;

$X^-$ is $Cl^-$ or an acetate anion ($CH_3COO^-$);

$X^-$ may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=3 is satisfied.]

[Chemical Formula 13]

[In Chemical Formula 13, $R^{93}$ is methyl, ethyl, isopropyl or tert-butyl;

$R^{94}$, $R^{95}$ and $R^{96}$ are each independently (C1-C20)alkyl;

n is an integer of 1 to 10, preferably 1 to 5;

X— is $Cl^-$ or an acetate anion ($CH_3COO$—);

X— may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=5 is satisfied.]

[Chemical Formula 14]

[In Chemical Formula 14, $R^{97}$ is methyl, ethyl, isopropyl or tert-butyl;

$R^{98}$, $R^{99}$ and $R^{100}$ are each independently (C1-C20)alkyl;

[Chemical Formula 15]

[In Chemical Formula 15, $R^{101}$ is methyl, ethyl, isopropyl or tert-butyl;

$R^{102}$, $R^{103}$, $R^{104}$, $R^{105}$ and $R^{106}$ are each independently (C1-C20)alkyl;

n is an integer of 1 to 10, preferably 1 to 5;

m is an integer of 1 to 10, preferably 1 to 5;

$X^-$ is $Cl^-$ or an acetate anion ($CH_3COO^-$);

$X^-$ may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=5 is satisfied.]

[Chemical Formula 16]

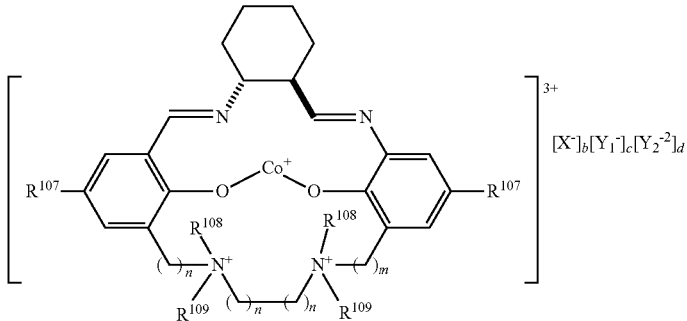

[In Chemical Formula 16,
$R^{107}$ is methyl, ethyl, isopropyl or tert-butyl;
$R^{108}$ and $R^{109}$ are each independently (C1-C20)alkyl;
n is an integer of 1 to 10, preferably 1 to 5;
m is an integer of 1 to 10, preferably 1 to 5;
$X^-$ is $Cl^-$ or an acetate anion ($CH_3COO^-$);
$X^-$ may be coordinated to Co;
$Y_1^-$ is $Cl^-$, $Br^-$ or $NO_3^-$;
$Y_2^{-2}$ is $SO_4^{-2}$; and
b is an integer of 1 or more, c is an integer of 0 or more, d is an integer of 0 or more, and b+c+2d=3 is satisfied.]

[Chemical Formula 17]

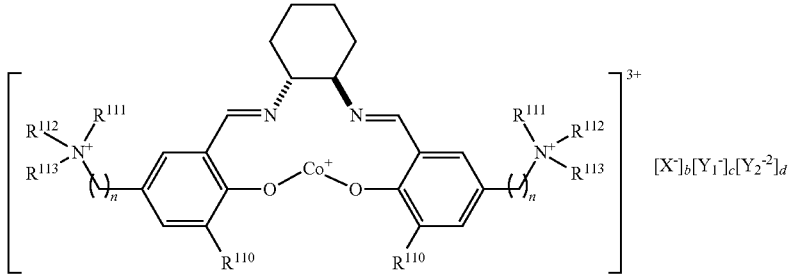

[In Chemical Formula 17,
$R^{100}$ is methyl, ethyl, isopropyl or tert-butyl;
$R^{111}$, $R^{112}$ and $R^{113}$ are each independently (C1-C20) alkyl;
n is an integer of 1 to 10, preferably 1 to 5;
$X^-$ is $Cl^-$ or an acetate anion ($CH_3COO^-$);
$X^-$ may be coordinated to Co;
$Y_1^-$ is $Cl^-$, $Br^-$ or $NO_3^-$;
$Y_2^{-2}$ is $SO_4^{-2}$; and
b is an integer of 1 or more, c is an integer of 0 or more, d is an integer of 0 or more, and b+c+2d=3 is satisfied.]

[Chemical Formula 18]

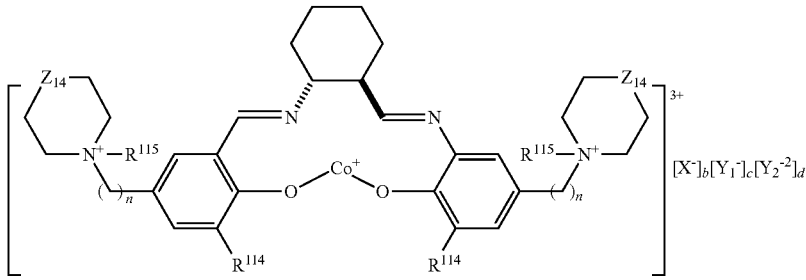

[In Chemical Formula 18,
R$^{114}$ is methyl, ethyl, isopropyl or tert-butyl;
R$^{115}$ is (C1-C20)alkyl;
Z$_{14}$ is an oxygen atom, a sulfur atom or a methylene group (—CH$_2$—);
n is an integer of 1 to 10, preferably 1 to 5;
X$^-$ is Cl$^-$ or an acetate anion (CH$_3$COO$^-$);
X$^-$ may be coordinated to Co;
Y$_1^-$ is Cl$^-$, Br$^-$ or NO$_3^-$;
Y$_2^{-2}$ is SO$_4^{-2}$; and
b is an integer of 1 or more, c is an integer of 0 or more, d is an integer of 0 or more, and b+c+2d=3 is satisfied.]

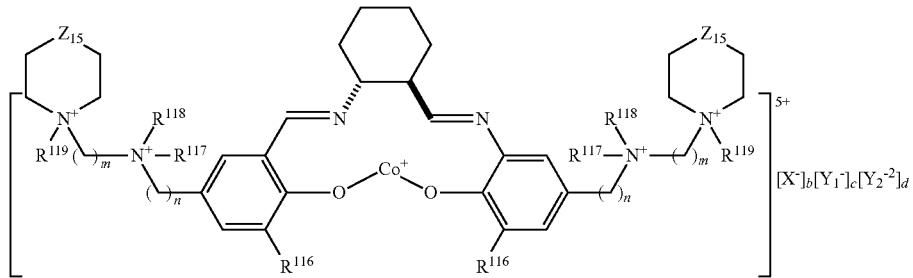

[Chemical Formula 19]

[In Chemical Formula 19,
R$^{116}$ is methyl, ethyl, isopropyl or tert-butyl;
R$^{117}$, R$^{118}$ and R$^{119}$ are each independently (C1-C20) alkyl;
Z$_{15}$ is an oxygen atom, a sulfur atom or a methylene group (—CH$_2$—);
n is an integer of 1 to 10, preferably 1 to 5;
m is an integer of 1 to 10, preferably 1 to 5;
X$^-$ is Cl$^-$ or an acetate anion (CH$_3$COO$^-$);
X$^-$ may be coordinated to Co;
Y$_1^-$ is Cl$^-$, Br$^-$ or NO$_3^-$;
Y$_2^{-2}$ is SO$_4^{-2}$; and
b is an integer of 1 or more, c is an integer of 0 or more, d is an integer of 0 or more, and b+c+2d=5 is satisfied.]

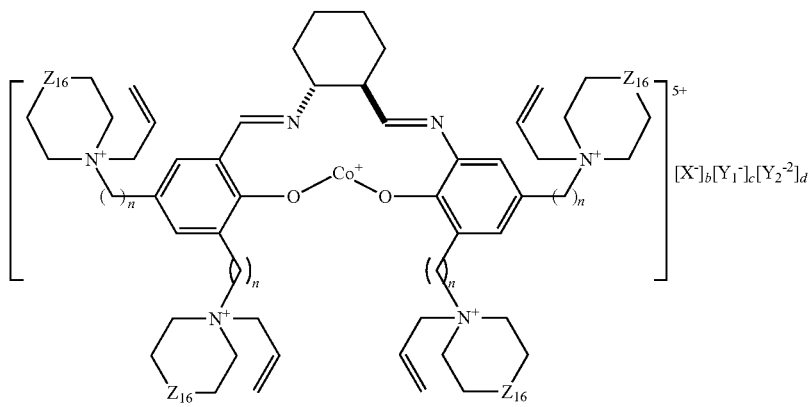

[Chemical Formula 20]

[In Chemical Formula 20, $Z_{16}$ is an oxygen atom, a sulfur atom or a methylene group (—$CH_2$—);

n is an integer of 1 to 10, preferably 1 to 5;

$X^-$ is $Cl^-$ or an acetate anion ($CH_3COO^-$);

$X^-$ may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=5 is satisfied.]

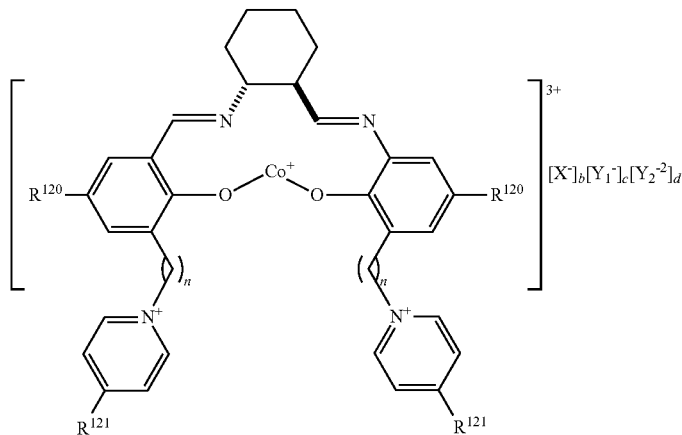

[Chemical Formula 21]

[In Chemical Formula 21, $R^{120}$ is methyl, ethyl, isopropyl or tert-butyl;

$R^{121}$ is hydrogen, methyl, ethyl, isopropyl or tert-butyl;

n is an integer of 1 to 10, preferably 1 to 5;

$X^-$ is $Cl^-$ or an acetate anion ($CH_3COO^-$);

$X^-$ may be coordinated to Co;

$Y_1^-$ is $Cl^-$, $Br^-$ or $NO_3^-$;

$Y_2^{-2}$ is $SO_4^{-2}$; and b is an integer of 1 or more, c is an integer of 0 or more, d is an integer of 0 or more, and b+c+2d=3 is satisfied.]

In addition, in the compound represented by Chemical Formula 9 which is a molecular weight regulator, a compound in which c is 1; and J is C1 to C60 hydrocarbyl radical with or without an ether group, an ester group, or an amine group may be used as a molecular weight regulator.

In addition, in the compound represented by Chemical Formula 9, a compound in which c is 2; and J is C1 to C60 hydrocarbyl diradical with or without an ether group, an ester group, or an amine group may be used as a molecular weight regulator, and specifically, the compound may be selected from a compound in which the structure of the compound represented by Chemical Formula 9 is $J(CO_2H)_2$ (J is —[$CR_2$]$_n$— (n is an integer from 0 to 20; and R which may be identical or different represents hydrogen, methyl, ethyl, propyl or butyl), para-phenylene, meta-phenylene, ortho-phenylene or 2,6-naphthalenediyl), or a compound in which the structure of the compound represented by Chemical Formula 9 is $J(OH)_2$ (J is —[$CR_2$]$_n$— (n is an integer from 0 to 20; and R which may be identical or different represents hydrogen, methyl, ethyl, propyl or butyl), —$CH_2CH_2N(R)CH_2CH_2$— (R is C1C20 hydrocarbyl), or —[$CH_2CH(R)O$]$_n$$CH_2CH(R)$— (n is an integer from 0 to 10; and R is hydrogen or methyl)), or a compound in which the structure of the compound represented by Chemical Formula 9 is OH—$C_6H_4$—$CO_2H$.

In addition, in the compound represented by Chemical Formula 9, a compound in which c is 3; and J is a C1-C60 hydrocarbyl triradical with or without an ether group, an ester group or an amine group may be used as a molecular weight regulator, and specifically, an example of the compound may include a compound in which the structure of the compound represented by Chemical Formula 9 is $J(CO_2H)_3$ (J is 1,2,3-propanetriyl, 1,2,3-benzenetriyl, 1,2,4-benzenetriyl or 1,3,5-benzenetriyl.

Further, in the compound represented by Chemical Formula 9, a compound in which c is 4; and J is a C1-C60 hydrocarbyl tetraradical with or without an ether group, an ester group or an amine group may be used as a molecular weight regulator, and specifically, an example of the compound may include a compound in which the structure of the compound represented by Chemical Formula 9 is $J(CO_2H)_4$ (1,2,3,4-butanetetrayl or 1,2,4,5-benzenetetrayl).

In addition, specific examples of the compound represented by Chemical Formula 9 may include adipic acid, ethanol, caproic acid, succinic acid, ethylene glycol, diethylene glycol, N-phenyl diethanol amine, 4-hydroxybenzoic acid, 1,2,3-propane tricarboxylic acid, 1,2,4-benzene tricarboxylic acid or 1,2,3,4-butanetetracarboxylic acid, and the like.

Specific examples of the epoxide compound in the preparation method according to the present invention include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxide-7-octene, epifluorohydrin, epichlorohydrin, epibromohydrin, isopropyl glycidyl ether, butyl glycidyl ether, tert-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxidenorbornene, limonene oxide, dieldrin, 2,3epoxidepropylbenzene, styrene oxide, phenylpropylene oxide, stilbene oxide, chlorostilbene oxide, dichlorostilbene oxide, 1,2-epoxy-3-phenoxypropane, benzyloxymethyl oxyrane, glycidyl-methylphenyl ether, chlorophenyl-2,3-epoxidepropyl ether, epoxypropyl methoxy phenyl ether, biphenyl glycidyl ether, glycidyl naphthyl ether, and the like.

The epoxide compound may be used in polymerization using an organic solvent as a reaction medium, and examples of the solvent include aliphatic hydrocarbons such as pentane, octane, decane, cyclohexane, and the like, aromatic hydrocarbons such as benzene, toluene, xylene, and the like, and halogenated hydrocarbons such as chloromethane, methylene chloride, chloroform, carbon tetrachloride, 1,1-dichloroethane, 1,2-dichloroethane, ethylchloride, trichloroethane, 1-chloropropane, 2-chloropropane, 1-chlorobutane, 2-chlorobutane, 1-chloro-2-methylpropane, chlorobenzene, bromobenzene, and the like, which may be used alone or in combination of two or more thereof. More preferably, bulk polymerization using a monomer itself as a solvent may be performed.

In the preparation method of the present invention, a molar ratio of the epoxide compound to catalyst may range from 500 to 1,000,000, preferably from 1,000 to 200,000. In addition, a molar ratio of the catalyst to the molecular weight regulator may range from 1 to 3,000, preferably from 5 to 2,000. In the preparation method of the present invention, pressure of carbon dioxide may be up to 100 bar, preferably, 5 bar to 50 bar. In the preparation method of the present invention, polymerization temperature may be from 10° C. to 120° C., preferably, 20° C. to 90° C.

The poly(alkylene carbonate) prepared by the preparation method of the present invention has a number average molecular weight ($M_n$) of 1,000 to 100,000 and a molecular weight distribution (that is, $M_w/M_n$, PDI) of 1.0 to 3.0. Here, $M_n$ indicates a number average molecular weight measured by GPC with calibration using polystyrene having a single molecular weight distribution as a standard material, and molecular weight distribution $M_w/M_n$ indicates a ratio between a weight average molecular weight and a number average molecular weight specified by GPC using the same method.

Meanwhile, since the preparation method of the present invention is characterized by using the novel complex as the catalyst, as another embodiment of the present invention, poly(alkylene carbonate) having high molecular weight may be prepared by copolymerization of carbon dioxide/epoxide only in the presence of the novel complex without addition of the molecular weight regulator.

The maximum turnover number (TON) which is capable of being implemented by the catalyst used in the preparation method of the present invention is about 10,000.

The poly(alkylene carbonate) prepared by the preparation method of the present invention may be preferably represented by the following Chemical Formula 22, and here, the —OH terminal group may be used to prepare polyurethane.

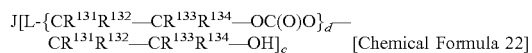    [Chemical Formula 22]

[In Chemical Formula 22,

L is —O— or —CO$_2$—;

c is an integer of 2 to 10, L may be identical or different;

J is C1-C60 hydrocarbyl c-valent radical with or without an ether group, an ester group or an amine group;

$R^{131}$ to $R^{134}$ are each independently hydrogen; (C1-C10) alkyl substituted or unsubstituted with halogen or (C1-C20) alkoxy; (C6-C12)aryl substituted or unsubstituted with halogen or (C1-C20)alkoxy and may be linked with each other to thereby form a ring; and a value obtained by multiplying d by c is a neutral number of 1000 or less.]

In other words, in the polymer compound represented by Chemical Formula 22, c is 2; J is C1-C60 hydrocarbyl diradical with or without an ether group, an ester group or an amine group; $R^{131}$ to $R^{134}$ are each independently hydrogen or methyl; d is an integer of 5 to 500, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 22 may be preferably a compound in which c is 2; L is —CO$_2$—; J is —[CR$_2$]$_n$— (n is an integer of 0 to 20; R which may be identical or different represents hydrogen, methyl, ethyl, propyl or butyl), para-phenylene, meta-phenylene, ortho-phenylene or 2,6-naphthalenediyl, or a compound in which c is 2; L is —O—; J is —[CR$_2$]$_n$— (n is an integer of 0 to 20; R which may be identical or different represents hydrogen, methyl, ethyl, propyl or butyl), —CH$_2$CH$_2$N(R)CH$_2$CH$_2$— (R is C1 to C20 hydrocarbyl) or —[CH$_2$CH(R)O]$_n$CH$_2$CH(R)— (n is an integer of 0 to 10; and R is hydrogen or methyl).

In other words, in the polymer compound represented by Chemical Formula 22, c is 3; J is C1-C60 hydrocarbyl diradical with or without an ether group, an ester group or an amine group; $R^{131}$ to $R^{134}$ are each independently hydrogen or methyl; d is a natural number of 330 or less, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 22 is preferably a compound in which c is 3; L is —CO$_2$—; and J is 1,2,3-propanetriyl, 1,2,3-benzenetriyl, 1,2,4-benzenetriyl or 1,3,5-benzenetriyl.

In other words, in the polymer compound represented by Chemical Formula 22, c is 4; J is C1-C60 hydrocarbyl diradical with or without an ether group, an ester group or an amine group; $R^{131}$ to $R^{134}$ are each independently hydrogen or methyl; d is a natural number of 250 or less, and preferably, all of $R^{131}$ to $R^{134}$ may be hydrogen or all of $R^{131}$ to $R^{133}$ may be hydrogen and $R^{134}$ may be methyl(in some repeated units, $R^{131}$ is methyl, and all of the remaining $R^{132}$ to $R^{134}$ are hydrogen).

The polymer compound represented by Chemical Formula 22 is preferably a compound in which c is 4; L is —CO$_2$—; and J is 1,2,3,4-butanetetrayl or 1,2,4,5-benzenetetrayl.

In the case where the polymer compound in which c is 3 or 4, which is a star shaped polymer having three or four branches, is used to prepare polyurethane, it may induce cross-linking and thus may be employed in preparation of thermosetting polyurethane.

The low molecular weight poly(alkylene carbonate) polymer prepared by the preparation method of the present invention may be used itself in a coating material, and the like, and may also be used in a blend with other polymers.

Advantageous Effects of Invention

The present invention provides the method of preparing low molecular weight of poly(alkylene carbonate) by copolymerization of carbon dioxide and epoxide using the molecular weight regulator in the presence of the novel complex, such that even though the molecular weight regulator is used, the activity of the catalyst may be stably maintained, whereby the low molecular weight of poly (alkylene carbonate) having a desirable level may be effectively provided.

In addition, it is expected that since the novel complex as the catalyst of the present invention has a simple structure as compared to the existing copolymerization catalyst, due to the economical preparation cost thereof, the novel complex may be effectively applied to a large-scale commercial process.

Further, since the novel complex of the present invention structurally includes at least two or more onium salts in a molecule, the complex used as a catalyst may have excellent activity and promote polymerization even at a relatively low temperature. In particular, in the case in which one or two or more onium salt(s) are symmetrically present at both sides based on a central metal, respectively, the preparation yield of the complex may be improved.

In addition, it is expected that the low molecular weight of poly(alkylene carbonate) prepared by the preparation method of the present invention may be effectively used even in preparing polyurethane.

DESCRIPTION OF THE INVENTION

Hereinafter, the following Examples and Comparative Examples specifically describe the effect of the present invention. However, Examples below are not intended to limit the scope of the present invention but only to exemplify the present invention.

The catalyst used in the present invention was prepared as shown below.

[Preparation Example 1] Synthesis of Compound 6

A symmetrical cobalt-salen catalyst 6 containing ammonium salt prepared by the following method was prepared.

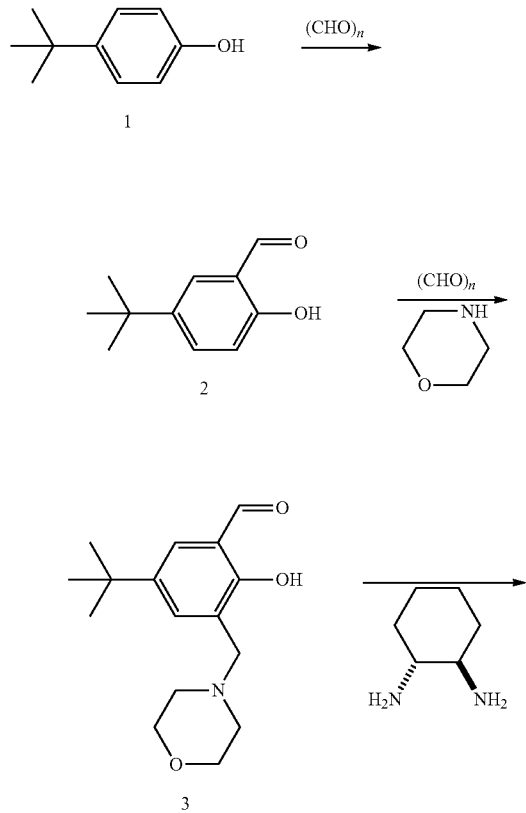

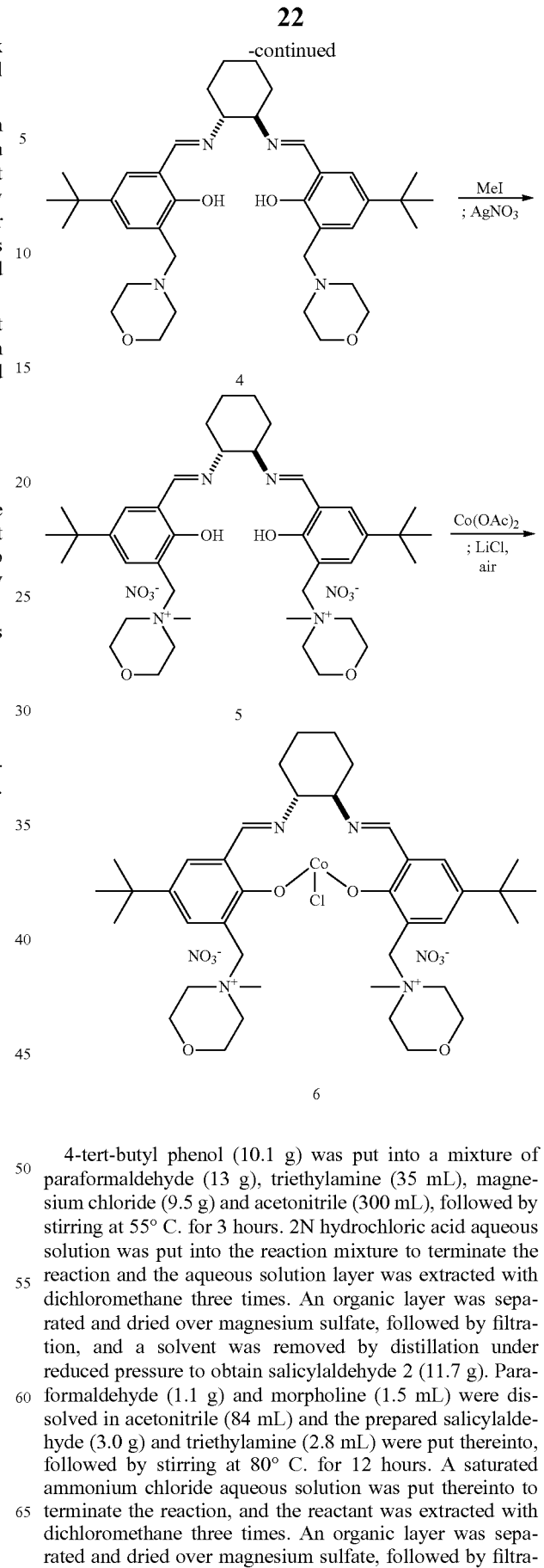

4-tert-butyl phenol (10.1 g) was put into a mixture of paraformaldehyde (13 g), triethylamine (35 mL), magnesium chloride (9.5 g) and acetonitrile (300 mL), followed by stirring at 55° C. for 3 hours. 2N hydrochloric acid aqueous solution was put into the reaction mixture to terminate the reaction and the aqueous solution layer was extracted with dichloromethane three times. An organic layer was separated and dried over magnesium sulfate, followed by filtration, and a solvent was removed by distillation under reduced pressure to obtain salicylaldehyde 2 (11.7 g). Paraformaldehyde (1.1 g) and morpholine (1.5 mL) were dissolved in acetonitrile (84 mL) and the prepared salicylaldehyde (3.0 g) and triethylamine (2.8 mL) were put thereinto, followed by stirring at 80° C. for 12 hours. A saturated ammonium chloride aqueous solution was put thereinto to terminate the reaction, and the reactant was extracted with dichloromethane three times. An organic layer was separated and dried over magnesium sulfate, followed by filtration and distillation under reduced pressure to obtain salicylaldehyde 3 containing morpholine (4.7 g). Prepared salicylaldehyde (4.7 g) and 1,2-trans-diaminocyclohexane (1.0 mL) were dissolved in ethanol (84 mL), followed by stirring at room temperature for 3 hours. After distillation under reduced pressure, the obtained reactant was recrystallized in a mixed solvent of n-hexane and dichloromethane to obtain a symmetrical salen derivative 4 (8.7 g). The prepared symmetrical salen derivative (1.5 g) was put into a round bottom flask wrapped with aluminum foil and was dissolved into acetonitrile (47 mL) and then iodomethane (0.4 mL) was put thereinto, followed by stirring at room temperature for 1 day. After removing a solvent by distillation under reduced pressure, the reactant was dissolved in ethanol (80 mL) again and silver nitrate (883 mg) was put thereinto, followed by stirring at 70° C. for 1.5 hours. The reaction solution was filtered and distilled under reduced pressure to obtain a symmetrical salen ligand 5 containing ammonium salt (2.0 g). The prepared ligand (2.0 g) was dissolved in methanol (48 mL), and cobalt acetate tetrahydrate (673 mg) was put thereinto, followed by stirring at room temperature for 12 hours, and then lithium chloride (305 mg) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 6 containing ammonium salt (1.3 g) was obtained. Result obtained by spectroscopy experiment of the symmetrical salen ligand containing ammonium salt was as follows.

$^1$H-NMR (500 MHz, DMSO-$d_6$) δ 14.56 (2H, br s), 8.63 (2H, s), 7.59 (2H, s), 7.57 (2H, s), 4.63 (2H, d, J=13.0 Hz), 4.54 (2H, d, J=13.0 Hz), 3.97-3.85 (8H, m), 3.63-3.29 (10H, m), 3.10 (6H, s), 1.95 (2H, br s), 1.81 (2H, br s), 1.63 (2H, br s), 1.47 (2H, br s), 1.21 (18H, s)

[Preparation Example 2] Synthesis of Compound 10

A symmetrical cobalt-salen catalyst 10 containing ammonium salt prepared by the following method was prepared

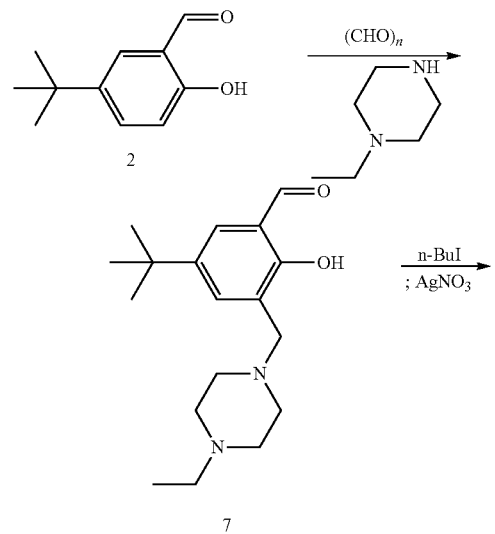

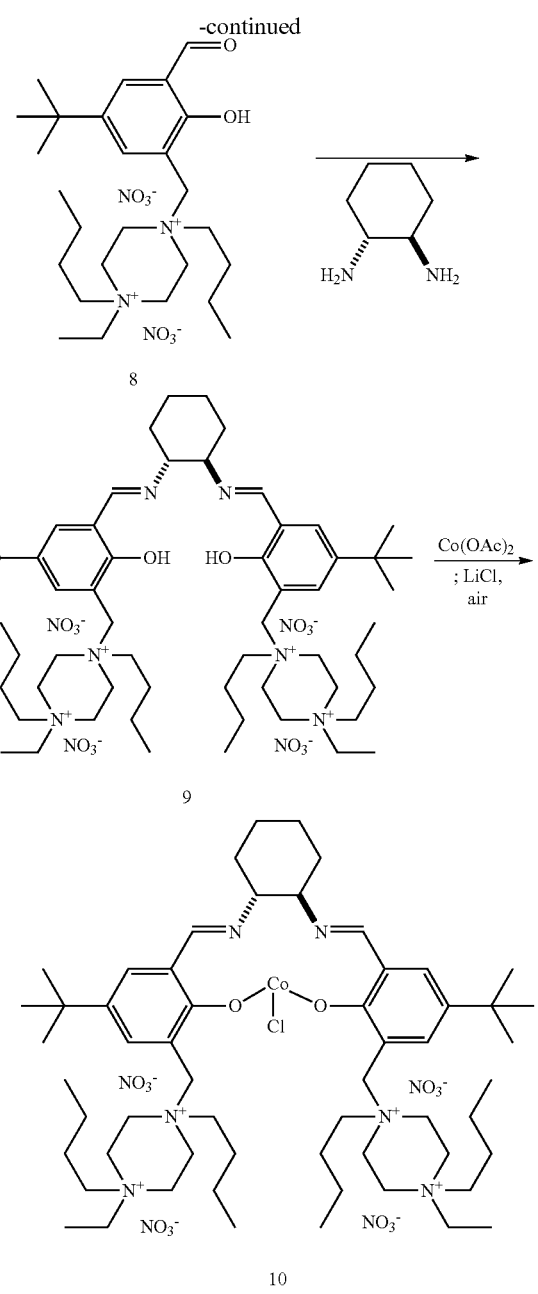

Paraformaldehyde (1.5 g) and N-ethylpiperazine (5.7 mL) were dissolved in ethanol (75 mL) and salicylaldehyde 2 (8.0 g) prepared by the same method as Preparation Example 1 was put thereinto, followed by stirring at 80° C. for 3 days. A saturated ammonium chloride aqueous solution was put thereinto to terminate the reaction, and the reactant was extracted with dichloromethane three times. An organic layer was separated, dried over sodium sulfate and filtered, and then a solvent was removed by distillation under reduced pressure and salicylaldehyde containing piperazine 7 (10.4 g) was obtained by column chromatography. The prepared salicylaldehyde derivative (6.1 g) was put into a round bottom flask wrapped with aluminum foil and was dissolved in acetonitrile (200 mL) and then iodobutane (23 mL) was put thereinto, followed by stirring at 80° C. for 1 day. The solvent was removed by distillation under reduced pressure and the reactant was dissolved in ethanol (670 mL)

again and silver nitrate (8.5 g) was put thereinto, followed by stirring at room temperature for 1 day. After the reaction solution was filtered, the solvent was removed by distillation under reduced pressure to obtain a salicylaldehyde derivative 8 containing ammonium salt (6.4 g). The prepared salicylaldehyde derivative containing ammonium salt (4.9 g) and 1,2-trans-diaminocyclohexane (0.6 mL) were dissolved into ethanol (45 mL), followed by stirring at room temperature for 1 day. The solvent was removed by distillation under reduced pressure and a mixed solvent of n-hexane and dichloromethane were put into the reactant again, followed by stirring at room temperature for 1 hour, and the reactant was filtered and dried to obtain a symmetrical salen derivative 9 (4.9 g). The prepared ligand (2.9 g) was dissolved in methanol (48 mL), and cobalt acetate tetrahydrate (697 mg) was put thereinto, followed by stirring at room temperature for 12 hours, and then lithium chloride (551 mg) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 10 containing ammonium salt (1.9 g) was obtained. Result obtained by spectroscopy experiment of the salicylaldehyde derivative containing ammonium salt was as follows.

$^1$H-NMR (500 MHz, CDCl$_3$) δ9.92 (1H, s), 7.54 (1H, s), 7.48 (1H, s), 3.73 (2H, s), 3.69-3.63 (4H, m), 3.50-3.47 (2H, m), 2.91 (4H, s), 1.46-1.37 (8H, m), 1.34-1.20 (8H, m), 1.27 (9H, s), 0.97-0.86 (6H, m)

[Preparation Example 3] Synthesis of Compound 15

A symmetrical cobalt-salen catalyst 15 containing ammonium salt prepared by the following method was prepared.

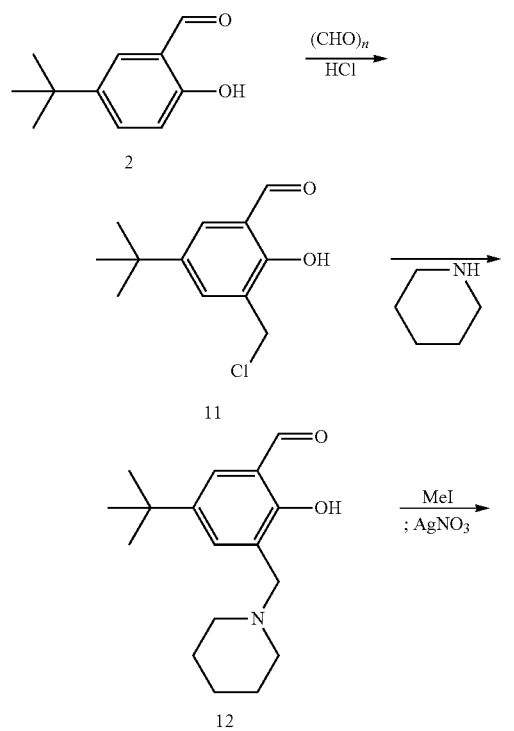

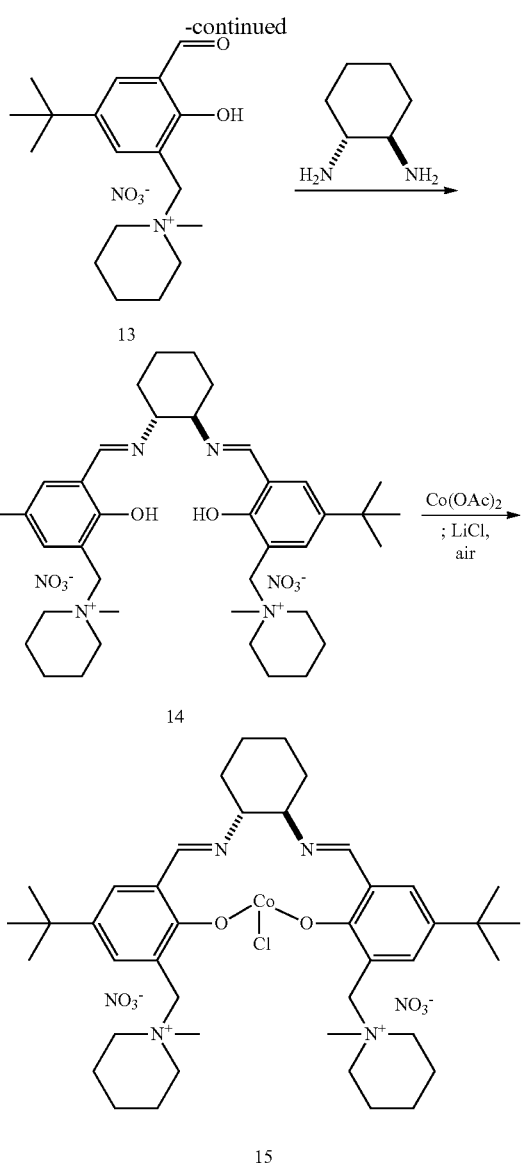

4-tert-butylsalicylaldehyde 2 (7.1 g) was put into a mixture of paraformaldehyde (3.6 g) and 1N hydrochloric acid aqueous solution (150 mL), followed by stirring at room temperature for 2 days. A saturated sodium bicarbonate aqueous solution was slowly put thereinto to neutralize the reactant, and the aqueous layer was extracted with dichloromethane. An organic layer was separated and dried over magnesium sulfate, followed by filtration, and the solvent was removed by distillation under reduced pressure to obtain chloromethyl salicylaldehyde 11 (7.0 g). After piperidine (2.9 g) was dissolved in acetonitrile (30 mL), the prepared chloromethyl salicylaldehyde (7.0 g) was put thereinto and stirred at room temperature for 3 hours. A saturated sodium bicarbonate aqueous solution was put thereinto to terminate the reaction, and the reactant was extracted with dichloromethane. An organic layer was separated and dried over sodium sulfate, followed by filtration, and a solvent was removed by distillation under reduced pressure to obtain salicylaldehyde 12 containing piperidine (8.0 g). The prepared salicylaldehyde derivative (8.0 g) was put into a round bottom flask wrapped with aluminum foil and was dissolved in acetonitrile (24 mL) and then iodomethane (5.4 mL) was put thereinto, followed by stirring at 40° C. for 1 day. After the solvent was removed by distillation under reduced pressure, the reactant was dissolved in ethanol (24 mL) again and silver nitrate (5.9 g) was put thereinto, followed by stirring at 70° C. for 1.5 hours. After the reaction solution was filtered, the reactant was distilled under reduced pressure to obtain salicylaldehyde 13 containing ammonium salt (9.2 g). The prepared salicylaldehyde (9.2 g) and 1,2-trans-diaminocyclohexane (1.5 g) were dissolved in ethanol (45 mL), followed by reflux stirring for 3 hours. After distillation under reduced pressure, the obtained reactant was recrystallized in a mixed solvent of n-hexane and dichloromethane to obtain a symmetrical salen ligand 14 (19.5 g). The prepared ligand (19.5 g) was dissolved in methanol (200 mL), and cobalt acetate tetrahydrate (6.8 g) was put thereinto, followed by stirring at room temperature for 12 hours, and then lithium chloride (1.3 g) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 15 containing ammonium salt (13.1 g) was obtained. Result obtained by spectroscopy experiment of the symmetrical salen ligand containing ammonium salt was as follows.

$^1$H-NMR (500 MHz, CDCl$_3$) δ 13.93 (2H, br s), 8.36 (2H, s), 7.58 (2H, s), 7.26 (2H, s), 4.24-4.21 (4H, m), 3.69-3.50 (6H, m), 3.41 (6H, s), 2.79-2.68 (4H, m), 2.04-1.21 (38H, m)

[Preparation Example 4] Synthesis of Compound 19

A symmetrical cobalt-salen catalyst 19 containing ammonium salt prepared by the following method was prepared.

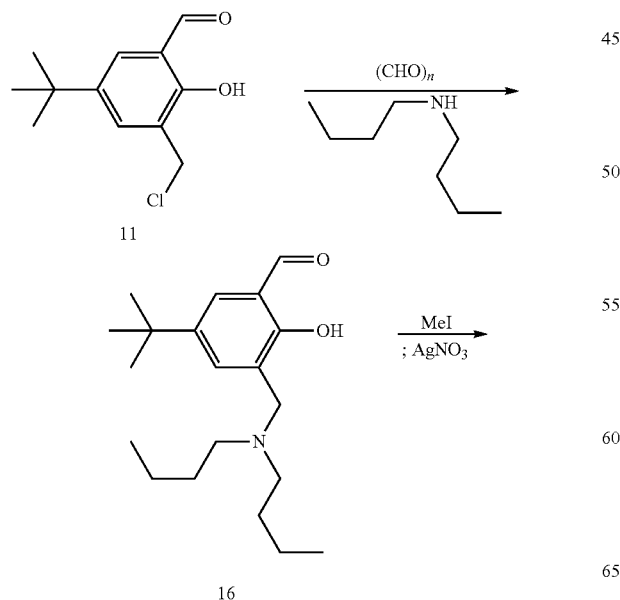

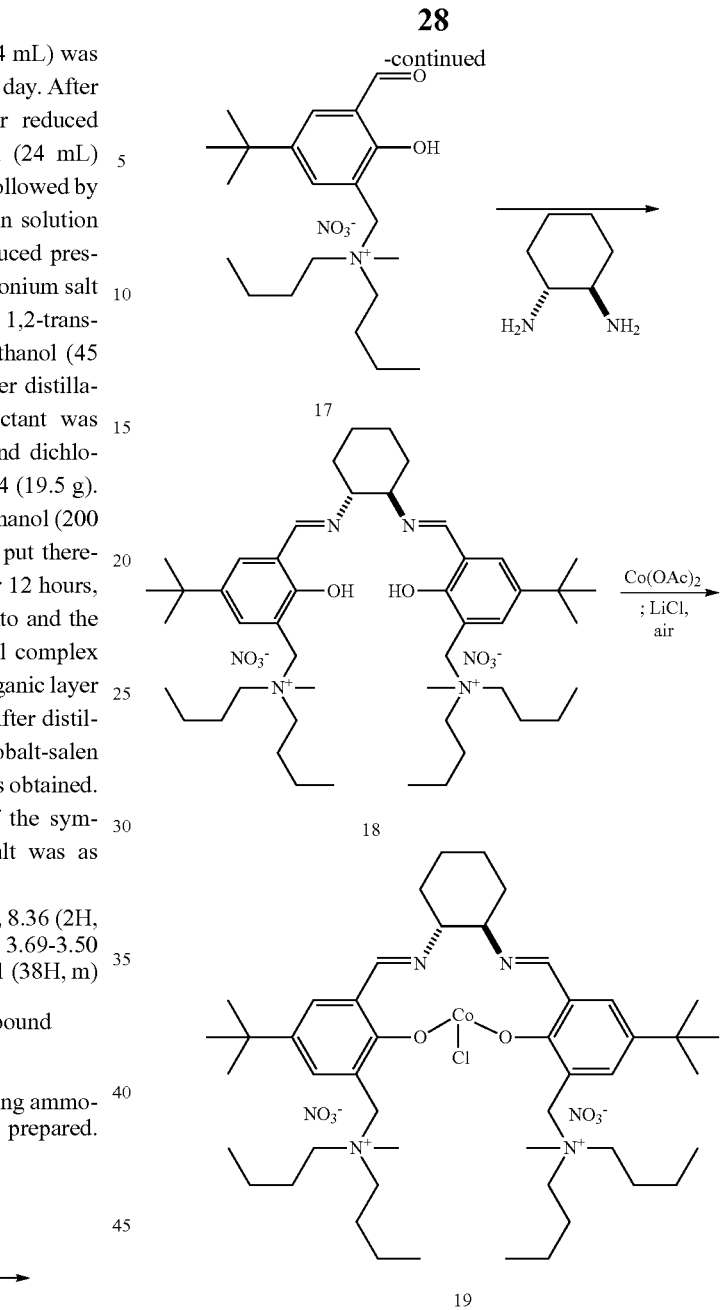

After dibutylamine (6.2 mL) was dissolved in acetonitrile (30 mL), the chloromethyl salicylaldehyde 11 (7.0 g) prepared by the same method as Preparation Example 3 was put thereinto and stirred at room temperature for 3 hours. A saturated sodium bicarbonate aqueous solution was put thereinto to terminate the reaction, and the reactant was extracted with dichloromethane. An organic layer was separated and dried over magnesium sulfate, followed by filtration and distillation under reduced pressure to obtain salicylaldehyde 16 containing dibutylamine (9.3 g). The prepared salicylaldehyde derivative (9.3 g) was put into a round bottom flask wrapped with aluminum foil and was dissolved in acetonitrile (24 mL) and then iodomethane (5.4 mL) was put thereinto, followed by stirring at 40° C. for 1 day. After the solvent was removed by distillation under reduced pressure, the reactant was dissolved in ethanol (24 mL) again and silver nitrate (5.9 g) was put thereinto, followed by stirring at 70° C. for 1.5 hours. After the reaction solution was filtered, the reactant was distilled under reduced pressure to obtain salicylaldehyde 17 containing ammonium salt (9.7 g). The prepared salicylaldehyde (9.7 g) and 1,2-trans-diaminocyclohexane (1.4 g) were dissolved in ethanol (45 mL), followed by reflux stirring for 3 hours. After distillation under reduced pressure, the obtained reactant was recrystallized in a mixed solvent of n-hexane and dichloromethane to obtain a symmetrical salen ligand 18 (19.6 g). The prepared ligand (19.6 g) was dissolved in methanol (200 mL), and cobalt acetate tetrahydrate (6.2 g) was put thereinto, followed by stirring at room temperature for 12 hours, and then lithium chloride (1.1 g) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 19 containing ammonium salt (12.3 g) was obtained. Result obtained by spectroscopy experiment of the symmetrical salen ligand containing ammonium salt was as follows.

$^1$H-NMR (500 MHz, DMSO-$d_6$) δ 8.58 (2H, s), 7.51 (2H, s), 7.43 (2H, s), 4.46 (4H, ABq, J=11.5, 6.5 Hz), 3.23 (2H, br s), 2.97 (6H, s), 2.88-2.51 (8H, m), 2.05-1.04 (42H, m), 0.97-0.78 (12H, m)

[Preparation Example 5] Synthesis of Compound 22

A symmetrical cobalt-salen catalyst 22 containing ammonium salt prepared by the following method was prepared.

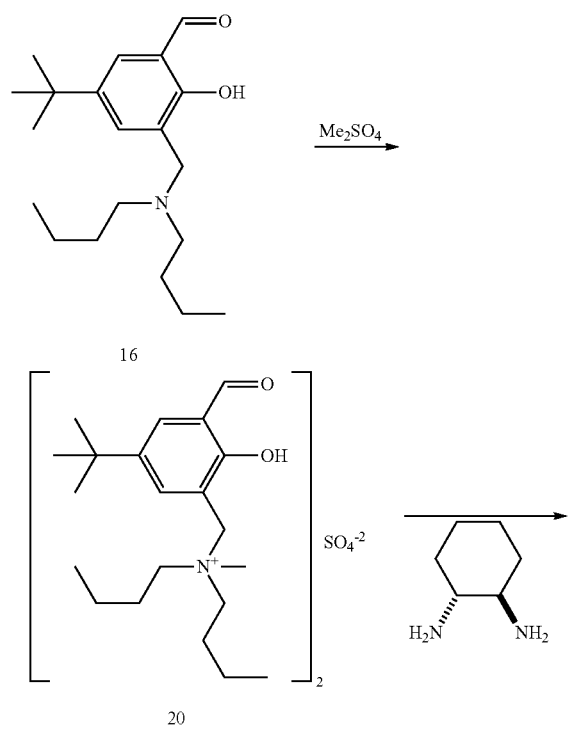

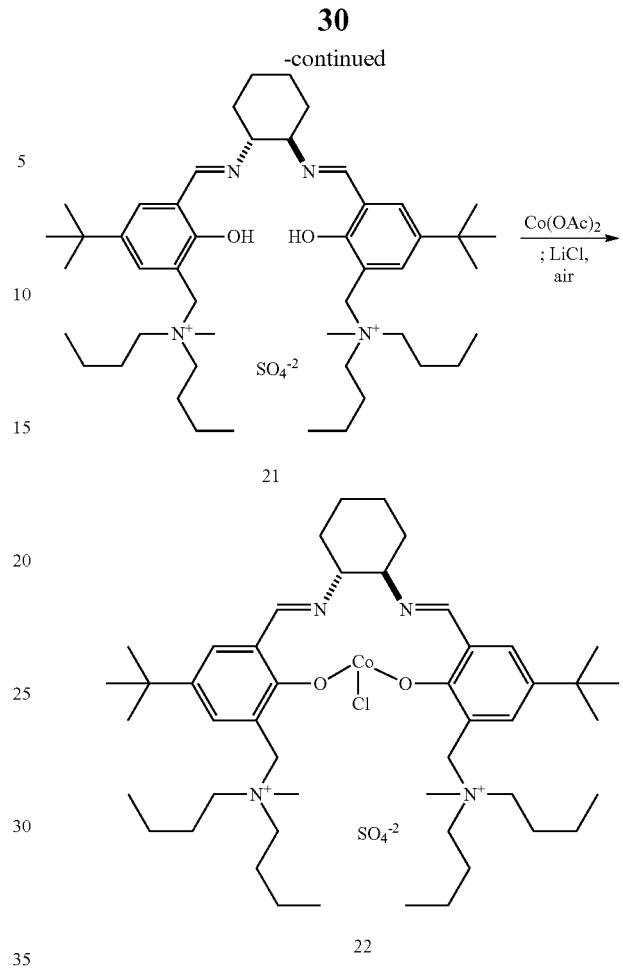

After the salicylaldehyde derivative 16 (9.3 g) prepared by the same method as Preparation Example 4 was dissolved in acetonitrile (30 mL), dimethyl sulfate (2.8 mL) was put thereinto, followed by stirring at room temperature for 1 day. A solvent was removed by distillation under reduced pressure to obtain salicylaldehyde 20 (11.5 g) containing ammonium salt. The prepared salicylaldehyde (11.5 g) and 1,2-trans-diaminocyclohexane (1.5 g) were dissolved in ethanol (45 mL), followed by reflux stirring for 3 hours. After distillation under reduced pressure, the obtained reactant was recrystallized in a mixed solvent of n-hexane and dichloromethane to obtain a symmetrical salen ligand 21 (20.3 g). The prepared ligand (20.3 g) was dissolved into methanol (200 mL), and cobalt acetate tetrahydrate (6.6 g) was put thereinto, followed by stirring at room temperature for 12 hours, and then lithium chloride (1.2 g) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 22 containing ammonium salt (16.0 g) was obtained. Result obtained by spectroscopy experiment of the symmetrical salen ligand containing ammonium salt was as follows.

$^1$H-NMR (500 MHz, CDCl$_3$) δ 8.39 (2H, s), 7.57 (2H, s), 7.30 (2H, s), 4.30 (4H, q, J=7.0 Hz), 3.77 (6H, s), 3.59 (2H, br s), 3.19-2.82 (8H, m), 2.01-1.21 (42H, m), 0.96-0.92 (12H, m)

[Preparation Example 6] Synthesis of Compound 26

A symmetrical cobalt-salen catalyst 26 containing ammonium salt prepared by the following method was prepared.

After dibutyl[2-(methylamino)ethyl]amine (6.8 g) was dissolved in acetonitrile (30 mL), the chloromethyl salicylaldehyde 11 (7.0 g) prepared by the same method as Preparation Example 3 was put thereinto and stirred at room temperature for 3 hours. A saturated sodium bicarbonate

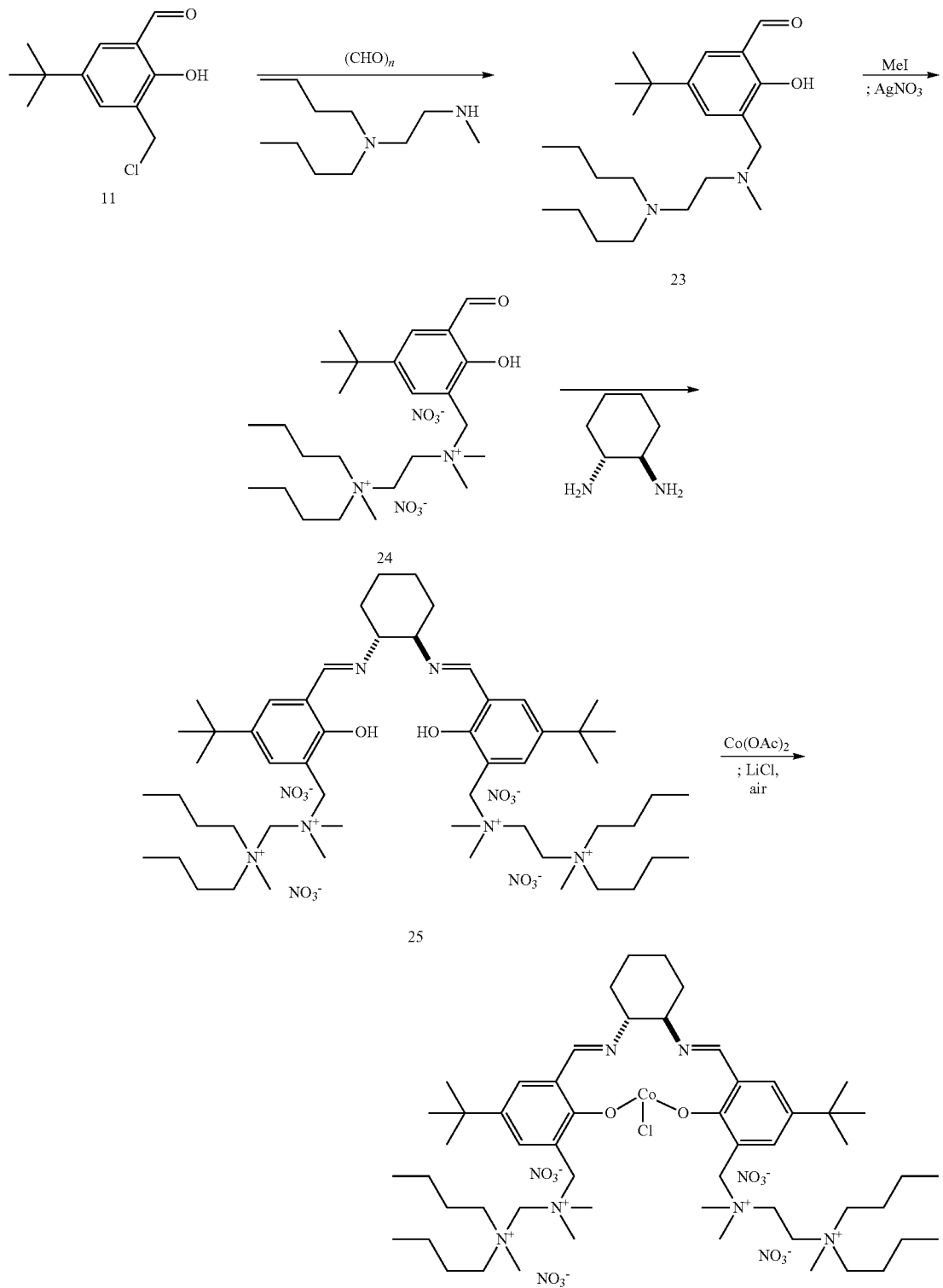

aqueous solution was put thereinto to terminate the reaction, and the reactant was extracted with dichloromethane. An organic layer was separated and dried over sodium sulfate, followed by filtration and distillation under reduced pressure to obtain salicylaldehyde 23 containing dibutyl[2-(methylamino)ethyl]amine (9.5 g). The prepared salicylaldehyde derivative (9.5 g) was put into a round bottom flask wrapped with aluminum foil and was dissolved in acetonitrile (30 mL) and then iodomethane (9.4 mL) was put thereinto, followed by stirring at 40° C. for 1 day. After the solvent was removed by distillation under reduced pressure, the reactant was dissolved in ethanol (30 mL) again and silver nitrate (10.2 g) was put thereinto, followed by stirring at 70° C. for 1.5 hours. After the reaction solution was filtered, the reactant was distilled under reduced pressure to obtain salicylaldehyde 24 containing ammonium salt (11.7 g). The prepared salicylaldehyde (11.7 g) and 1,2-trans-diaminocyclohexane (1.3 g) were dissolved in ethanol (45 mL), followed by reflux stirring for 3 hours. After distillation under reduced pressure, the obtained reactant was recrystallized in a mixed solvent of n-hexane and dichloromethane to obtain a symmetrical salen ligand 25 (21.9 g). The prepared ligand (21.9 g) was dissolved in methanol (200 mL), and cobalt acetate tetrahydrate (5.3 g) was put thereinto, followed by stirring at room temperature for 12 hours, and then lithium chloride (1.0 g) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 26 containing ammonium salt (15.4 g) was obtained. Result obtained by spectroscopy experiment of the symmetrical cobalt-salen containing ammonium salt was as follows.

$^1$H-NMR (500 MHz, DMSO-d$_6$) δ 8.06 (2H, s), 7.58 (2H, s), 7.51 (2H, s), 5.01 (2H, d, J=11.5 Hz), 4.90 (2H, d, J=11.5 Hz), 3.73 (4H, q, J=7.0 Hz), 3.58 (2H, br s), 3.51 (2H, s), 3.33 (12H, s), 3.26 (2H, s), 3.06-2.99 (8H, m), 1.98-1.56 (14H, m), 1.85 (6H, s), 1.28 (18H, s), 1.26-1.19 (10H, m), 0.98-0.86 (12H, m)

[Preparation Example 7] Synthesis of Compound 31

A symmetrical cobalt-salen catalyst 31 containing ammonium salt prepared by the following method was prepared.

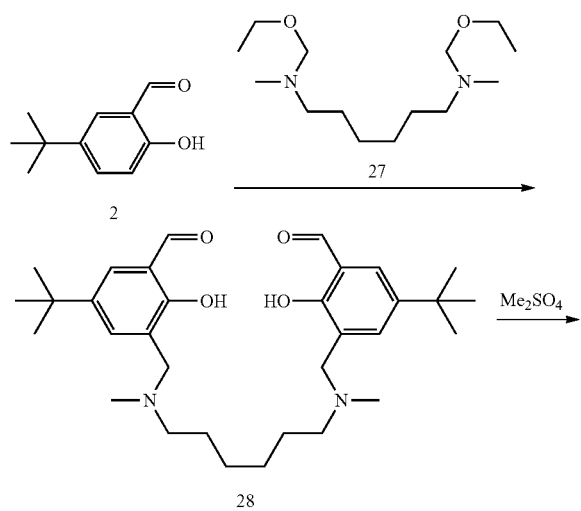

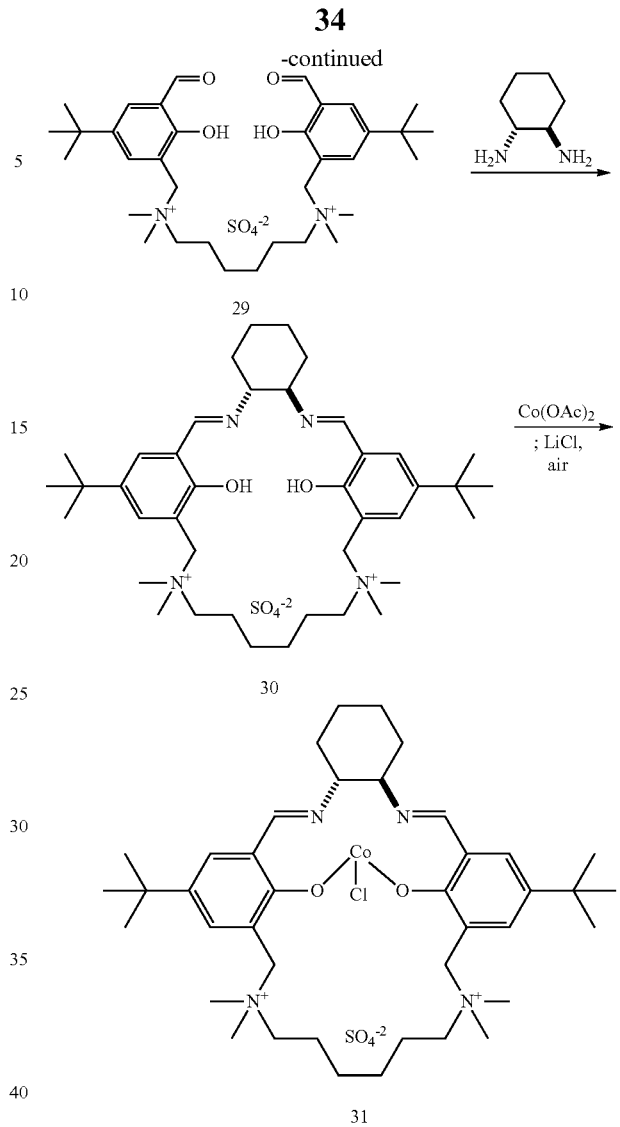

N,N'-dimethylhexane1,6diamine (2.6 g) was put into a mixture of potassium carbonate (5.5 g), paraformaldehyde (2.2 g) and ethanol (20 mL) and the mixture was stirred at room temperature for 3 days. A solid was removed by filtration and the reactant was distilled under reduced pressure to obtain a hexyldiamine derivative 27 substituted with ethoxymethyl group (4.2 g). The prepared hexyldiamine derivative (4.2 g) was dissolved in acetonitrile (40 mL) and 4-tert-butyl-salicylaldehyde 2 (5.8 g) prepared by the same method as Preparation Example 1 was put thereinto, followed by reflux stirring for 1 day, to obtain symmetrical salicylaldehyde 28 (6.1 g). After dimethyl sulfate (1.1 mL) was dissolved in acetonitrile (20 mL), the prepared symmetrical salicylaldehyde (6.1 g) was put thereinto and stirred at room temperature for 1 day. A solvent was removed by distillation under reduced pressure and a symmetrical salicylaldehyde 29 (6.6 g) was obtained. Result obtained by spectroscopy experiment of the salicylaldehyde linked with N,N'-dimethylhexane-1,6-diamine was as follows.

$^1$H-NMR (500 MHz, CDCl$_3$) δ 11.20 (2H, br s), 10.38 (2H, s), 7.64 (2H, s), 7.38 (2H, s), 3.74 (4H, s), 2.51-2.50 (4H, m), 2.31 (6H, s), 1.59 (4H, br s), 1.37-1.30 (4H, m), 1.28 (18H, s)

The prepared symmetrical salicylaldehyde derivative (6.6 g) and 1,2-trans-diaminocyclohexane (1.2 g) were dissolved in ethanol (35 mL), followed by reflux stirring for 3 hours. After distillation under reduced pressure, the obtained reactant was recrystallized in a mixed solvent of n-hexane and dichloromethane to obtain a symmetrical salen ligand 30 (6.6 g). The prepared ligand (6.6 g) was dissolved in methanol (200 mL), and cobalt acetate tetrahydrate (2.5 g) was put thereinto, followed by stirring at room temperature for 12 hours, and then lithium chloride (460 mg) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 31 containing an ammonium salt (5.7 g) was obtained. Result obtained by spectroscopy experiment of the symmetrical salen ligand containing ammonium salt was as follows.

$^{1}$H-NMR (500 MHz, CDCl$_{3}$) δ 13.47 (2H, br s), 8.27-8.25 (2H, m), 7.32-6.81 (4H, m), 3.73 (4H, q, J=6.5 Hz), 2.89-2.80 (2H, m), 2.44-2.43 (4H, m), 2.41 (6H, s), 2.22 (6H, s), 1.87-0.97 (34H, m)

[Preparation Example 8] Synthesis of Compounds 35 and 36

Symmetrical cobalt-salen catalysts 35 and 36 containing ammonium salt prepared by the following method were prepared.

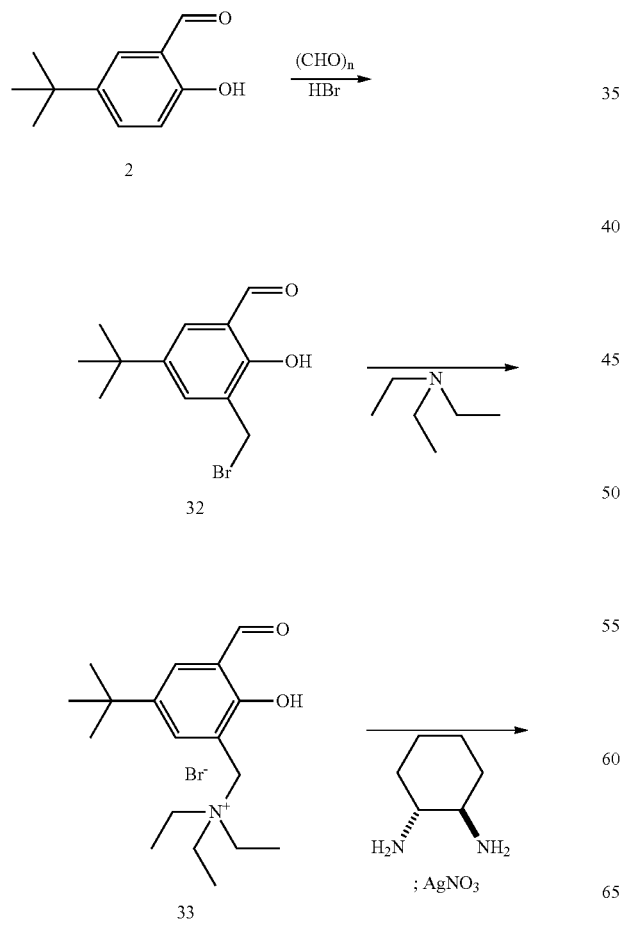

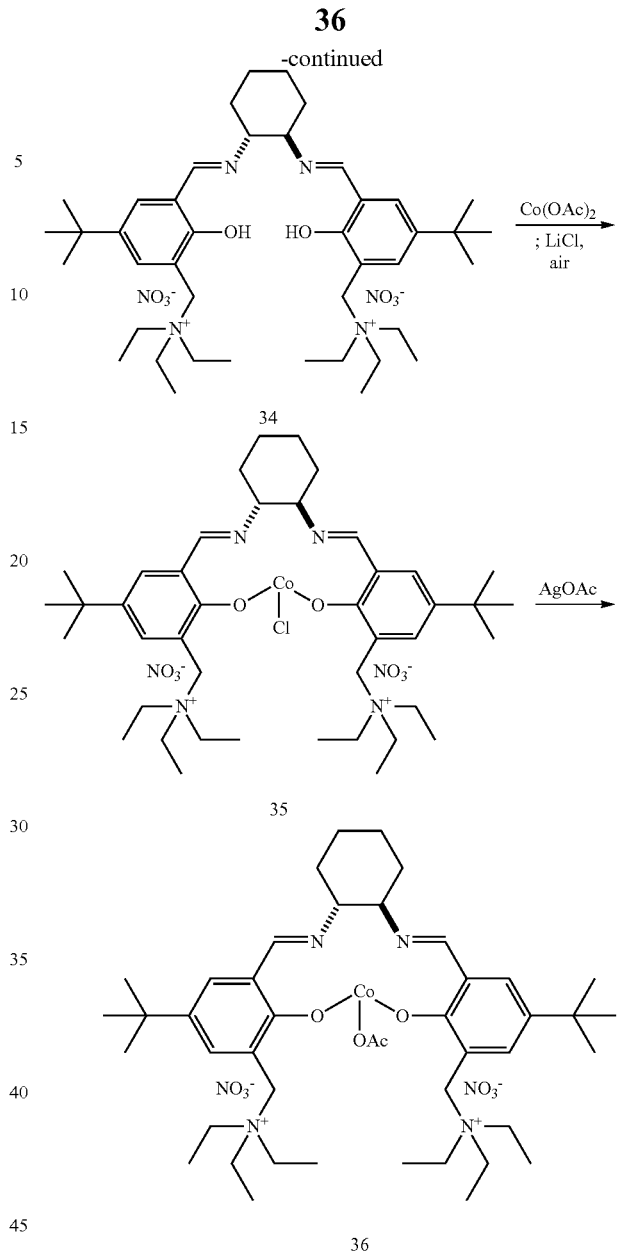

Salicylaldehyde 2 (3.1 g) prepared by the same method as Preparation Example 1, paraformaldehyde (0.8 g), 48% aqueous hydrogen bromide solution (15 mL), a catalytic amount of concentrated sulfuric acid was mixed together and stirred at 70° C. for 20 hours. After the reactant was cooled at room temperature, dichloromethane was put thereinto and extracted with water, the solvent was removed by distillation under reduced pressure, and bromomethyl salicylaldehyde 32 (4.4 g) was obtained. The prepared salicylaldehyde (1.5 g) was dissolved in toluene (20 mL), followed by stirring and triethylamine (1.5 g) was slowly put thereinto, followed by stirring at room temperature for 12 hours. The obtained solid was filtered and washed with toluene and n-hexane, respectively and then dried in vacuo to obtain salicylaldehyde 33 (1.7 g) containing ammonium salt was obtained. The obtained salicylaldehyde (1.4 g) was dissolved in ethanol (20 mL) and 1,2-trans-diaminocyclohexane (220 mg) was put thereinto, followed by reflux stirring for 5 hours. After cooling to room temperature, silver nitrate (420 mg) was put thereinto, followed by stirring at room temperature for 15 hours. After the obtained solid was filtered and removed, the solution was distilled under reduced pressure to remove a solvent to obtain a ligand 34 containing ammonium salt (1.3 g). The prepared ligand (1.0 g) was dissolved in methanol (50 mL), and cobalt acetate (240 mg) was put thereinto, followed by stirring at room temperature for 18 hours, and then lithium chloride (240 mg) was put thereinto and the reactant was oxidized by air. The obtained metal complex was dissolved into dichloromethane again and an organic layer was extracted with water to remove impurities. After distillation under reduced pressure, a symmetrical cobalt-salen catalyst 35 containing an ammonium salt (0.7 g) was obtained. The catalyst containing chlorine (0.7 g) was dissolved in dichloromethane (55 mL) again and silver acetate (240 mg) was put thereinto, followed by stirring for 3 hours, and the obtained solid was filtered and removed. After a solvent was removed by distillation under reduced pressure, a symmetrical cobalt-salen catalyst 36 containing acetate (0.7 g) was obtained. Result obtained by spectroscopy experiment of the symmetrical salen ligand containing ammonium salt was as follows.

$^1$H-NMR (500 MHz, DMSO-d6) δ 13.54 (2H, s), 8.51 (2H, s), 7.32 (2H, s), 7.25 (2H, s), 4.38 (4H, s), 3.06-3.04 (12H, m), 1.85-1.11 (28H, m), 0.90-0.88 (18H, m)

[Preparation Example 9] Synthesis of Compound 40

A symmetrical cobalt-salen catalyst 40 containing ammonium salt prepared by the following method was prepared.

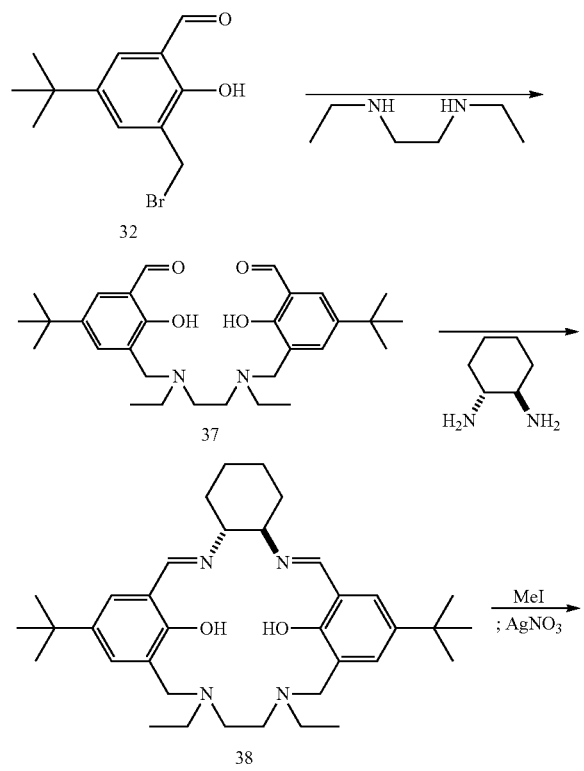

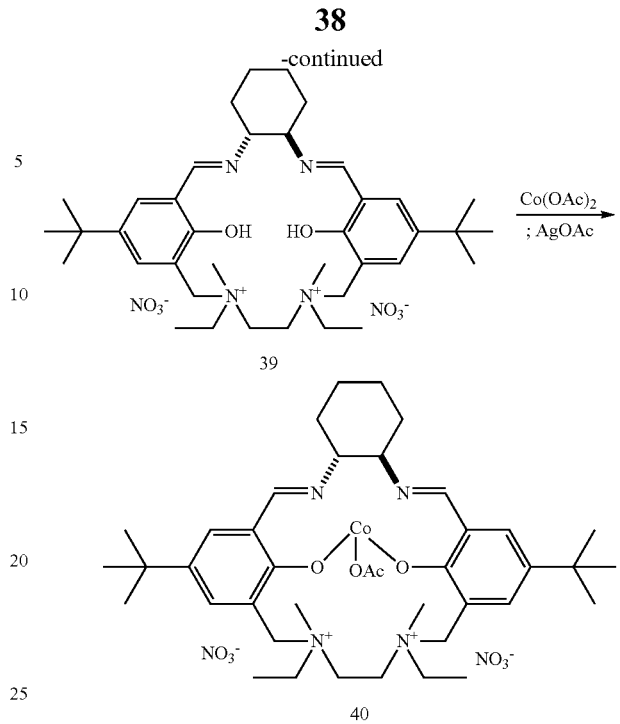

Bromomethyl salicylaldehyde 32 (1.5 g) prepared by the same method as Preparation Example 8 was dissolved in dichloromethane (3 mL) and triethylamine (1.1 g) and N,N'-diethylethylenediamine (0.3 g) was sequentially and slowly put thereinto. The reactant was stirred at room temperature for 20 hours, and extracted with water. The reactant was dried over magnesium sulfate, followed by filtration, and a solvent was removed by distillation under reduced pressure to obtain disalicylaldehyde 37 (0.7 g). Result obtained by spectroscopy experiment of the salicylaldehyde derivative was as follows.

$^1$H-NMR (500 MHz, CDCl$_3$) δ 11.32 (2H, br s), 9.89 (2H, s). 7.64 (2H, d, J=2.4 Hz), 7.53 (2H, d, J=2.5 Hz). 3.67 (4H, s), 2.66-2.56 (8H, m), 1.20-0.98 (24H, m)

The prepared disalicylaldehyde (0.7 g) and 1,2-trans-diaminocyclohexane (0.3 g) were dissolved in ethanol (12 mL), followed by reflux stirring for 5 hours. A solvent was removed by distillation under reduced pressure, and a symmetrical salen derivative 38 (960 mg) was obtained. The prepared symmetrical salen derivative (960 mg) was put into a round bottom flask wrapped with aluminum foil and was dissolved in acetonitrile (25 mL) and then iodomethane (2.5 mL) was put thereinto, followed by stirring at room temperature for 18 hours. After the solvent was removed by distillation under reduced pressure, the reactant was dissolved in ethanol (22 mL) and silver nitrate (407 mg) was put thereinto, followed by stirring at room temperature for 15 hours. The reaction solution was filtered and distilled under reduced pressure to obtain a symmetrical salen ligand 39 containing ammonium salt (1.1 g). The prepared ligand (1.0 g) was put into a round-bottom flask wrapped with aluminum foil and dissolved into dichloromethane (25 mL) under a nitrogen atmosphere, and cobalt acetate (220 mg) was put thereinto, followed by stirring at room temperature for 5 hours. After the reactant was exposed to air, silver acetate (210 mg) was put thereinto, followed by stirring at room temperature for 4 hours, a solid was removed by filtration and a solvent was removed by distillation under reduced pressure, thereby obtaining a symmetrical cobalt-salen catalyst 40 (1.0 g) containing ammonium salt. Result obtained by spectroscopy experiment of the symmetrical salen ligand containing ammonium salt was as follows.

$^1$H-NMR (500 MHz, DMSO-$d_6$) δ 13.64 (2H, s), 8.48 (2H, s), 7.23 (2H, s), 7.13 (2H, s), 3.53 (6H, s), 3.37 (4H, s), 2.43-2.32 (8H, m), 1.86-1.23 (10H, m), 1.20-0.98 (24H, m)

[Preparation Example 10] Synthesis of Compound 47

A symmetrical cobalt-salen catalyst 47 containing ammonium salt prepared by the following method was prepared.

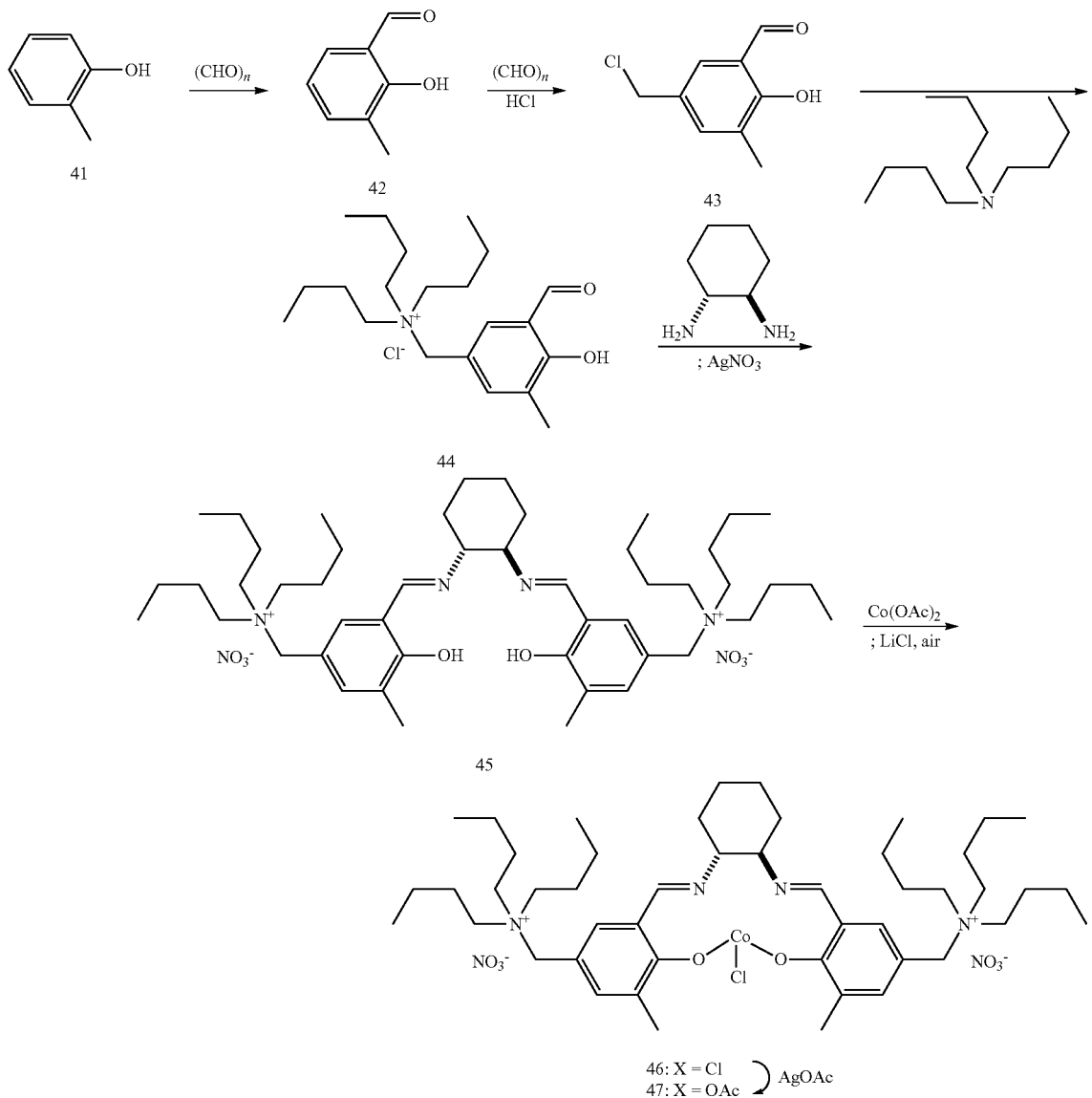

2-methylphenol (10.1 g) was dissolved in toluene (300 mL) and paraformaldehyde (20.3 g), magnesium chloride (17.7 g) and triethylamine (49.9 mL) were put thereinto, followed by reflux stirring at 130° C. for 5 hours. After the reactant was cooled at room temperature, 2N hydrochloric acid aqueous solution (100 mL) was put thereinto, followed by stirring 1 hour. After layer separation, the aqueous solution layer was extracted with ethyl acetate once and the combined organic layer was extracted with water and a saturated sodium bicarbonate aqueous solution, respectively. Magnesium sulfate was put into the organic layer, followed by stirring and filtration, and the solvent was removed by distillation under reduced pressure, and then the salicylaldehyde 42 (13.0 g) was obtained. The prepared salicylaldehyde (4.5 g), paraformaldehyde (1.3 g), 12 N hydrochloric acid aqueous solution (70 mL) was mixed and stirred at room temperature for 12 hours. After the obtained solid was filtered and dissolved in diethylether (50 mL) again and then extracted with water and a saturated sodium bicarbonate aqueous solution, respectively. Magnesium sulfate was put into the organic layer, followed by stirring and filtration, and the solvent was removed by distillation under reduced pressure, and then the salicylaldehyde 43 (3.6 g) containing chloromethyl was obtained. The prepared chloromethyl salicylaldehyde (1.0 g) was dissolved in toluene (20 mL), followed by stirring and tributylamine (1.5 g) was slowly put thereinto, followed by stirring at room temperature for 12 hours. The resulting solid was filtered and washed with toluene and n-hexane, respectively and then dried in vacuo to obtain the salicylaldehyde 44 (1.84 g) containing ammonium salt was obtained. Result obtained by spectroscopy experiment of the salicylaldehyde derivative was as follows.

$^1$H-NMR (500 MHz, DMSO-d$_6$) δ 10.96 (1H, br s), 10.05 (1H, s), 7.54 (1H, s), 7.43 (1H, s), 4.38 (2H, s), 2.99-2.95 (6H, m), 2.19 (3H, s), 1.66-1.60 (6H, m), 1.34-1.28 (6H, m), 0.89 (9H, t, J=5.6 Hz)

The obtained salicylaldehyde (1.5 g) was dissolved in ethanol (20 mL) and 1,2-trans-diaminocyclohexane (0.2 g) was put thereinto, followed by reflux stirring for 5 hours. After cooling to room temperature, silver nitrate (0.45 g) was put thereinto, followed by stirring at room temperature for 15 hours. After the obtained solid was filtered and removed, the solution was distilled under reduced pressure to remove a solvent to obtain a ligand 45 containing ammonium salt (1.46 g). The prepared ligand (993 mg) was dissolved in methanol (50 mL), and cobalt acetate (240 mg) was put thereinto, followed by stirring at room temperature for 18 hours, and then lithium chloride (240 mg) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 46 containing ammonium salt (870 mg) was obtained. The catalyst containing chlorine (870 mg) was dissolved in dichloromethane (50 mL) again and silver acetate (220 mg) was put thereinto, followed by stirring for 3 hours, and the obtained solid was filtered and removed. After a solvent was removed by distillation under reduced pressure, a symmetrical cobalt-salen catalyst 47 containing acetate (770 mg) was obtained. Result obtained by spectroscopy experiment of the symmetrical salen ligand containing ammonium salt was as follows.

$^1$H-NMR (500 MHz, DMSO-d$_6$) δ 13.60 (2H, s), 8.47 (2H, s), 7.10 (4H, s), 4.26 (4H, s), 2.80 (12H, s), 2.10 (6H, s), 1.86-1.79 (6H, m), 1.56-1.53 (12H, m), 1.51-1.38 (4H, m), 1.31-1.27 (12H, m), 0.89 (18H, t, J=5.6 Hz)

[Preparation Example 11] Synthesis of Compound 52

A symmetrical cobalt-salen catalyst 52 containing ammonium salt prepared by the following method was prepared.

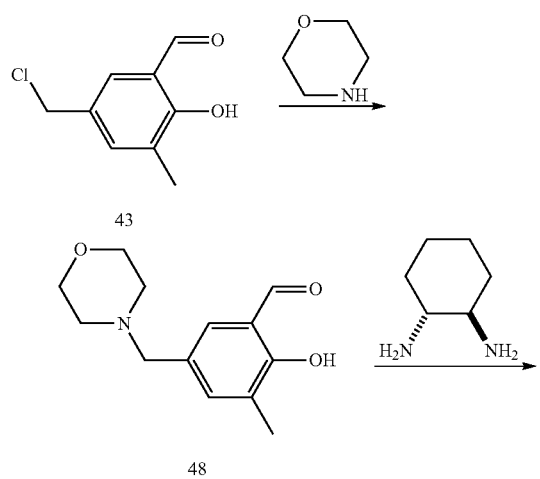

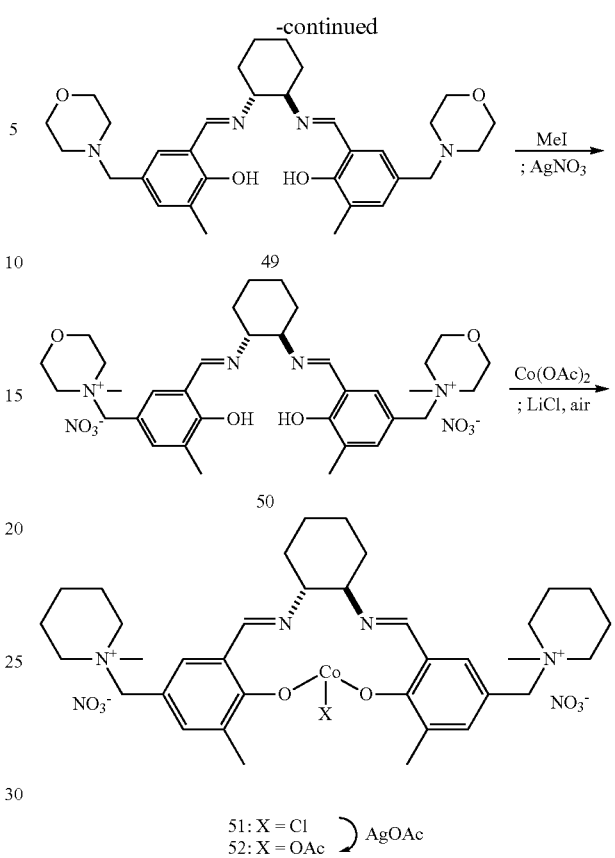

Chloromethyl salicylaldehyde 43 (1.2 g) prepared by the same method as Preparation Example 10 was dissolved in acetonitrile (30 mL), followed by stirring and triethylamine (1.2 mL) and morpholine (1.2 g) were slowly put thereinto, followed by stirring at room temperature 20 hours. After the reaction was completed by adding water thereto, the aqueous solution layer was extracted with ethyl acetate, an organic layer was dried over magnesium sulfate, followed by filtration and distillation under reduced pressure to remove a solvent, thereby obtaining salicylaldehyde 48 (1.4 g) containing morpholine. The prepared salicylaldehyde (1.4 g) was dissolved in ethanol (30 mL), and then 1,2-trans-diaminocyclohexane (0.3 g) was put thereinto, followed by reflux stirring for 5 hours. After the reactant was cooled at room temperature and distilled under reduced pressure to remove a solvent, a salen derivative 49 (1.4 g) was obtained. The prepared salen derivative (1.1 g) was put into a round bottom flask wrapped with aluminum foil and was dissolved in acetonitrile (30 mL) and then iodomethane (0.3 mL) was put thereinto, followed by stirring at room temperature for 18 hours. After the solvent was removed by distillation under reduced pressure, the reactant was dissolved in ethanol (28 mL) again and silver nitrate (503 mg) was put thereinto, followed by stirring at room temperature for 15 hours. After the obtained solid was filtered and removed, the solution was distilled under reduced pressure to remove a solvent, thereby obtaining a ligand 50 containing ammonium salt (1.24 g). The prepared ligand (0.8 g) was dissolved in methanol (50 mL), and cobalt acetate (240 mg) was put thereinto, followed by stirring at room temperature for 18 hours, and then lithium chloride (240 mg) was put thereinto and the reactant was oxidized by air. The obtained metal complex was dissolved in dichloromethane again and an organic layer was extracted with water to remove impurities. After distillation under reduced pressure, a symmetrical cobalt-salen catalyst 51 containing ammonium salt (680 mg) was obtained. The catalyst containing chlorine (679 mg) was dissolved into dichloromethane (50 mL) again and silver acetate (220 mg) was put thereinto, followed by stirring for 3 hours, and the obtained solid was filtered and removed. After a solvent was removed by distillation under reduced pressure, a symmetrical cobalt-salen catalyst 52 containing acetate (679 mg) was obtained. Result obtained by spectroscopy experiment of the symmetrical salen ligand containing ammonium salt was as follows.

$^1$H-NMR (500 MHz, DMSO-$d_6$) δ 14.18 (2H, s), 8.59 (2H, s), 7.41 (2H, s), 7.37 (2H, s), 4.56 (4H, s), 3.93-3.92 (8H, m), 3.37-3.32 (14H, m), 2.12 (6H, s), 1.93-1.47 (10H, m)

[Preparation Example 12] Synthesis of Compound 57

A symmetrical cobalt-salen catalyst 57 containing ammonium salt prepared by the following method was prepared.

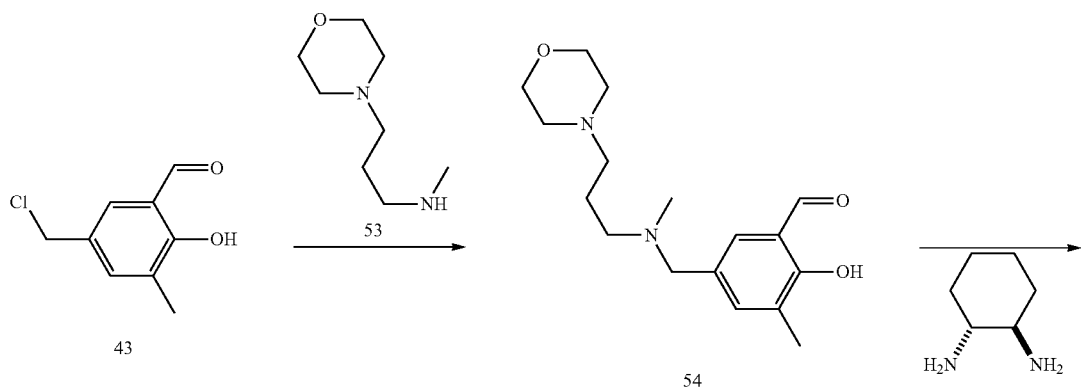

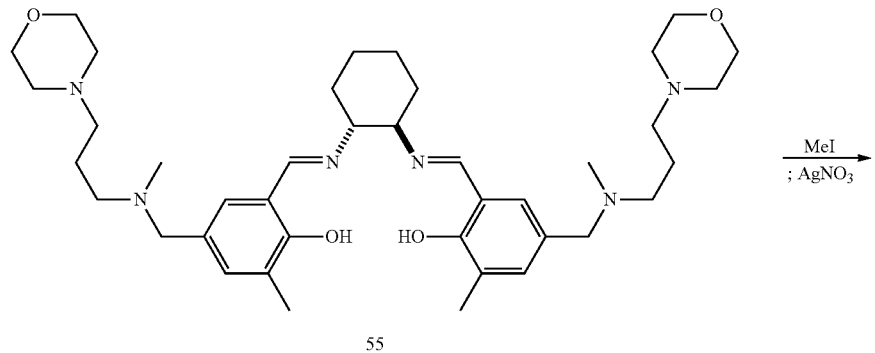

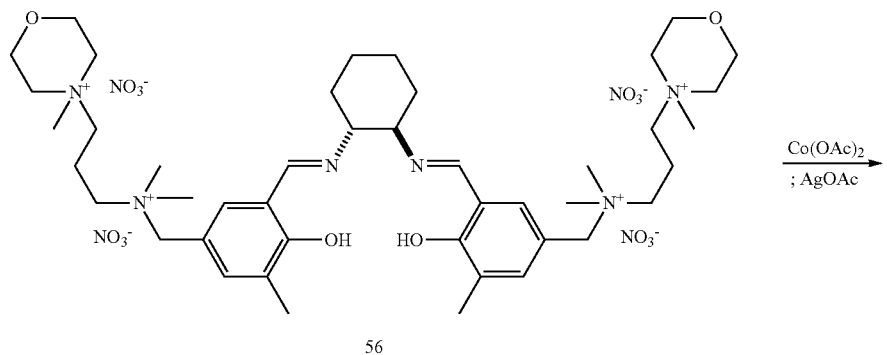

-continued

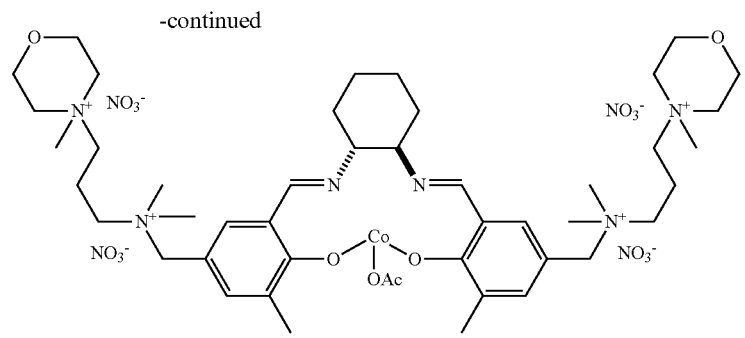

57

3-morpholin propylene amine (2.5 g) was dissolved in dichloromethane (40 mL) and triethylamine (3.6 mL) was put thereinto and the reactant was cooled at −20° C. Methyl chloroformate (2.0 mL) was slowly put thereinto and a temperature was slowly raised to room temperature. After the reactant was stirred for 3 hours, 0.1 N hydrochloric acid aqueous solution was put thereinto and an organic layer was separated and extracted with water and a saturated sodium bicarbonate aqueous solution, respectively. The reactant was dried over magnesium sulfate, filtered, and distilled under reduced pressure to remove a solvent. A mixture of lithium aluminum hydride (1.9 g) and tetrahydrofuran (18 mL) was cooled at 0° C. under a nitrogent atmosphere, and a mixture of the prepared carbamate (3.4 g) and tetrahydrofuran (18 mL) was slowly put thereinto. A temperature was raised and the reactant was reflux stirred for 4 hours and cooled at 0° C. and diluted with diethyl ether (12 mL). The reactant was strongly stirred and then water (1.6 mL), 15% sodium hydroxide aqueous solution (1.6 mL), water (4.8 mL) were sequentially and slowly put thereinto, followed by stirring for 5 hours. The obtained solid was filtered and removed, followed by distillation under reduced pressure, to thereby obtain a methylamine derivative 53 (2.6 g). Result obtained by spectroscopy experiment of the methylamine derivative was as follows.

$^1$H-NMR (500 MHz, CDCl$_3$) δ 3.72 (4H, t, J=4.0 Hz), 2.63-2.57 (2H, m), 2.42-2.37 (9H, m), 1.72-1.64 (3H, m)

Chloromethyl salicylaldehyde 43 (1.2 g) prepared by the same method as Preparation Example 10 was dissolved in acetonitrile (30 mL), followed by stirring and triethylamine (1.2 mL) and the prepared methylamine (2.3 g) were slowly put thereinto, followed by stirring at room temperature 20 hours. After the reaction was completed by adding water thereto, the aqueous solution layer was extracted with ethyl acetate, an organic layer was dried over magnesium sulfate, followed by filtration and distillation under reduced pressure to remove a solvent, thereby obtaining salicylaldehyde 54 (1.5 g) containing amine. The prepared salicylaldehyde (1.2 g) was dissolved in ethanol (20 mL) and 1,2-trans-diamino-cyclohexane (217 mg) was put thereinto, followed by reflux stirring for 5 hours. After the reactant was cooled at room temperature and distilled under reduced pressure to remove a solvent, a salen derivative 55 (1.1 g) was obtained. The prepared salen derivative (1.4 g) was put into a round bottom flask wrapped with aluminum foil and was dissolved in acetonitrile (30 mL) and then iodomethane (0.3 mL) was put thereinto, followed by stirring at room temperature for 18 hours. After the solvent was removed by distillation under reduced pressure, the reactant was dissolved in ethanol (26 mL) again and silver nitrate (483 mg) was put thereinto, followed by stirring at room temperature for 15 hours. After the obtained solid was filtered and removed, the solution was distilled under reduced pressure to remove a solvent, thereby obtaining a ligand 56 containing ammonium salt (1.87 g). The prepared ligand (1.1 g) was put into a roundbottom flask wrapped with aluminum foil and dissolved in dichloromethane (25 mL) under a nitrogen atmosphere, and cobalt acetate (182 mg) was put thereinto, followed by stirring at room temperature for 5 hours. After the reactant was exposed to air, silver acetate (182 mg) was put thereinto, followed by stirring at room temperature for 4 hours, a solid was removed by filtration and a solvent was removed by distillation under reduced pressure, thereby obtaining a symmetrical cobalt-salen catalyst 57 (1.0 g) containing ammonium salt. Result obtained by spectroscopy experiment of the symmetrical salen ligand containing ammonium salt was as follows.

$^1$H-NMR (500 MHz, DMSO-d$_6$) δ 14.20 (2H, s), 8.63 (2H, s), 7.42 (4H, d, J=18.0 Hz), 4.51 (4H, s), 3.95 (8H, s), 3.51-3.48 (14H, m), 3.21-3.19 (8H, m), 3.00-2.89 (12H, m), 2.34-2.19 (4H, m), 2.16 (6H, s), 1.88-1.48 (10H, m)

[Preparation Example 13] Synthesis of Compound 60

A symmetrical cobalt-salen catalyst 60 containing ammonium salt prepared by the following method was prepared.

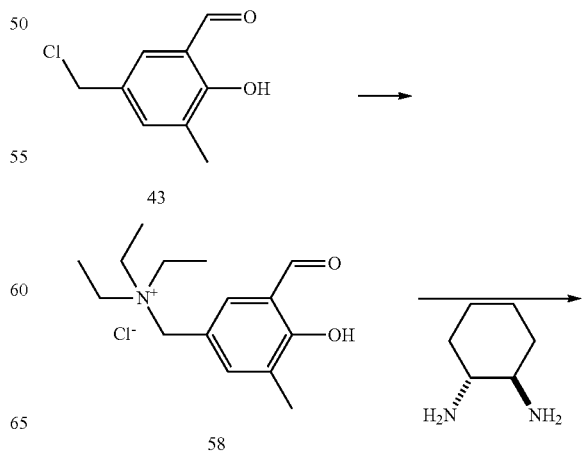

58

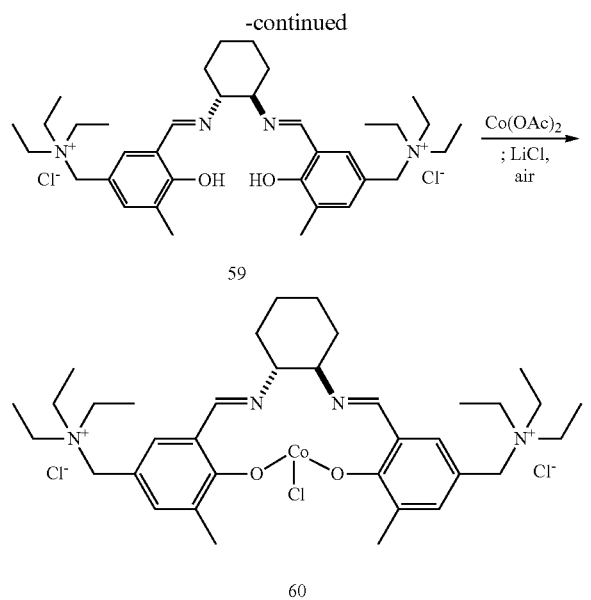

Chloromethyl salicylaldehyde 43 (1.2 g) prepared by the same method as Preparation Example 10 was dissolved in toluene (40 mL), followed by stirring and triethylamine (2.4 g) was slowly put thereinto, followed by stirring at room temperature 12 hours. The resulting solid was filtered and washed with toluene and n-hexane, respectively and then dried in vacuo to obtain salicylaldehyde 58 (2.8 g) containing ammonium salt was obtained. Result obtained by spectroscopy experiment of the salicylaldehyde derivative was as follows.

$^1$H-NMR (500 MHz, CDCl$_3$) δ 11.35 (1H, s), 9.95 (1H, s), 7.53 (1H, s), 7.42 (1H, s), 5.02 (2H, s), 3.77-3.12 (6H, m), 2.23 (3H, s), 1.49-1.44 (9H, m)

The obtained salicylaldehyde (1.1 g) was dissolved in ethanol (20 mL) and 1,2-trans-diaminocyclohexane (217 mg) was put thereinto, followed by reflux stirring for 5 hours. After the reactant was cooled at room temperature and distilled under reduced pressure to remove a solvent, a salen derivative 59 (1.1 g) was obtained. The prepared ligand (741 mg) was dissolved in methanol (50 mL) and cobalt acetate (240 mg) was put thereinto, followed by stirring at room temperature for 18 hours, and lithium chloride (240 mg) was put thereinto and the reactant was oxidized by air. The resulting metal complex was dissolved in dichloromethane again and an organic layer was extracted with water to remove impurities. After distillation under reduced pressure, a symmetrical cobalt-salen catalyst 60 containing ammonium salt (592 mg) was obtained. Result obtained by spectroscopy experiment of the symmetrical salen ligand containing ammonium salt was as follows.

$^1$H-NMR (500 MHz, DMSO-d$_6$) δ 13.20 (2H, s), 8.57 (2H, s), 7.22 (4H, s), 4.35 (4H, s), 2.96-2.64 (12H, m), 2.22 (6H, s), 1.90-1.45 (10H, m), 0.98 (18H, t, J=5.6 Hz)

[Preparation Example 14] Synthesis of Compound 65

A symmetrical cobalt-salen catalyst 65 containing ammonium salt prepared by the following method was prepared.

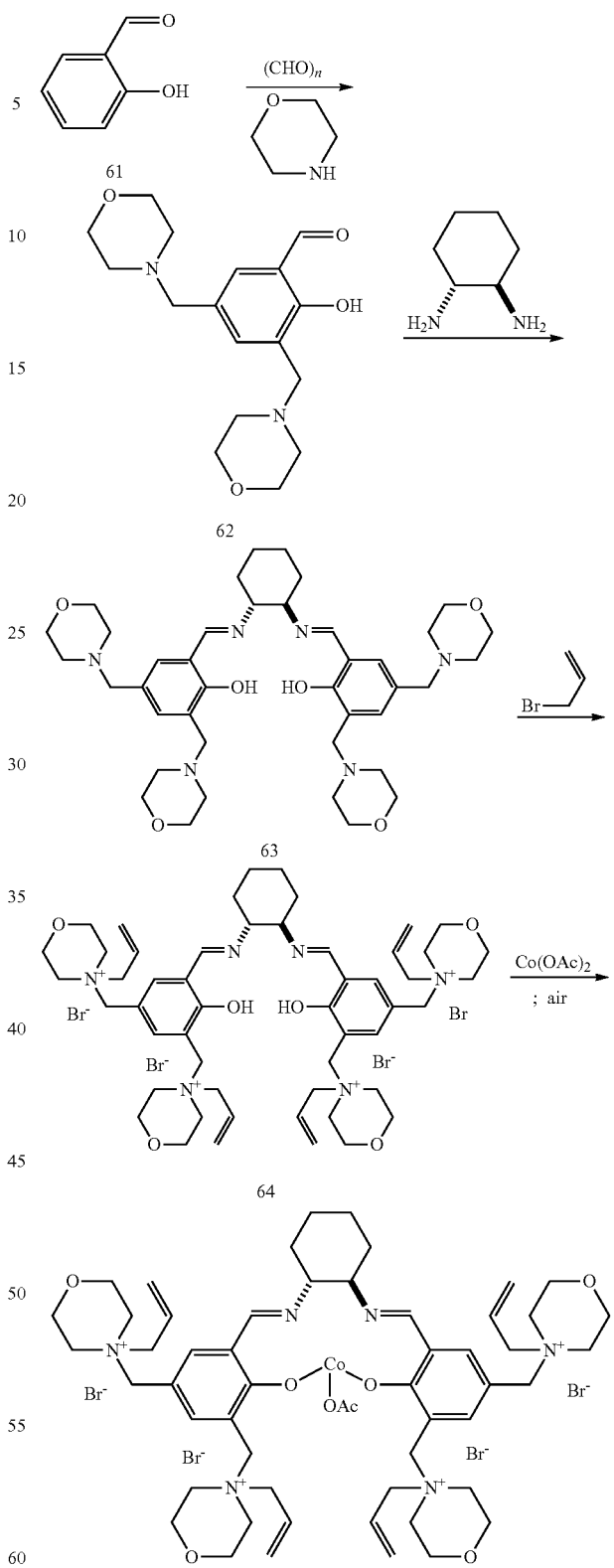

Salicylaldehyde (11.5 g) was dissolved in ethanol (100 mL), paraformaldehyde (6.2 g) and morpholine (18.0 g) were put thereinto, followed by stirring at 80° C. for 24 hours. A solvent was removed by distillation under reduced pressure and the reactant was dissolved in dichloromethane again and extracted with water and saturated sodium chloride aqueous solution. An organic layer was dried over magnesium sulfate, followed by filtration, and a solvent was removed by distillation under reduced pressure to obtain a salicylaldehyde derivative 62 (27.4 g). The prepared salicylaldehyde derivative (1.2 g) was dissolved in ethanol (20 mL) and 1,2-trans-diaminocyclohexane (217 mg) was put thereinto, followed by reflux stirring for 5 hours. After the reactant was cooled at room temperature and distilled under reduced pressure to remove a solvent, salen 63 (1.1 g) containing amine was obtained. Result obtained by spectroscopy experiment of the salen was as follows.

$^1$H-NMR (500 MHz, DMSO-d$_6$) δ 13.64 (2H, s), 8.48 (2H, s), 7.23 (2H, s), 7.13 (2H, s), 3.54-3.52 (16H, m), 3.39-3.36 (8H, m), 2.36 (4H, s), 2.34-2.31 (8H, m), 2.25 (4H, s), 1.88-1.09 (10H, m)

The prepared salen (0.6 g) was completely dissolved in acetonitrile (50 mL) and then allyl bromide (2.0 g) was slowly put thereinto. The reactant was stirred at room temperature for 18 hours and a solvent was removed by distillation under reduced pressure, a ligand 64 (1.0 g) was obtained. After the prepared ligand (1.0 mg) was put into a round-bottom flask wrapped with aluminum foil and dissolved in dichloromethane (20 mL) under a nitrogen atmosphere, cobalt acetate (142 mg) was put thereinto, and the reactant was exposed in the air, followed by stirring at room temperature for 5 hours. After a solvent was removed by distillation under reduced pressure, a symmetrical cobalt-salen catalyst 65 containing ammonium salt (0.9 g) was obtained. Result obtained by spectroscopy experiment of the symmetrical salen ligand containing ammonium salt was as follows.

$^1$H-NMR (500 MHz, DMSO-d$_6$) δ 13.94 (2H, s), 8.48 (2H, s), 7.25 (2H, s), 7.15 (2H, s), 4.59-4.56 (4H, m), 3.92-3.87 (8H, m), 3.52-3.43 (24H, m), 3.07 (8H, s), 2.36 (8H, s), 2.24 (8H, s), 1.92-1.32 (10H, m)

[Preparation Example 15] Synthesis of Compound 68

A symmetrical cobalt-salen catalyst 68 containing ammonium salt prepared by the following method was prepared.

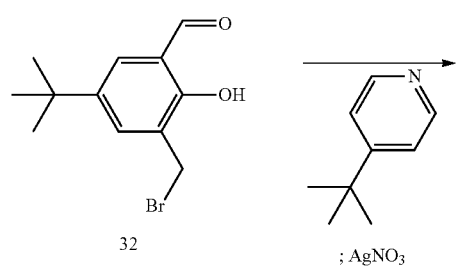

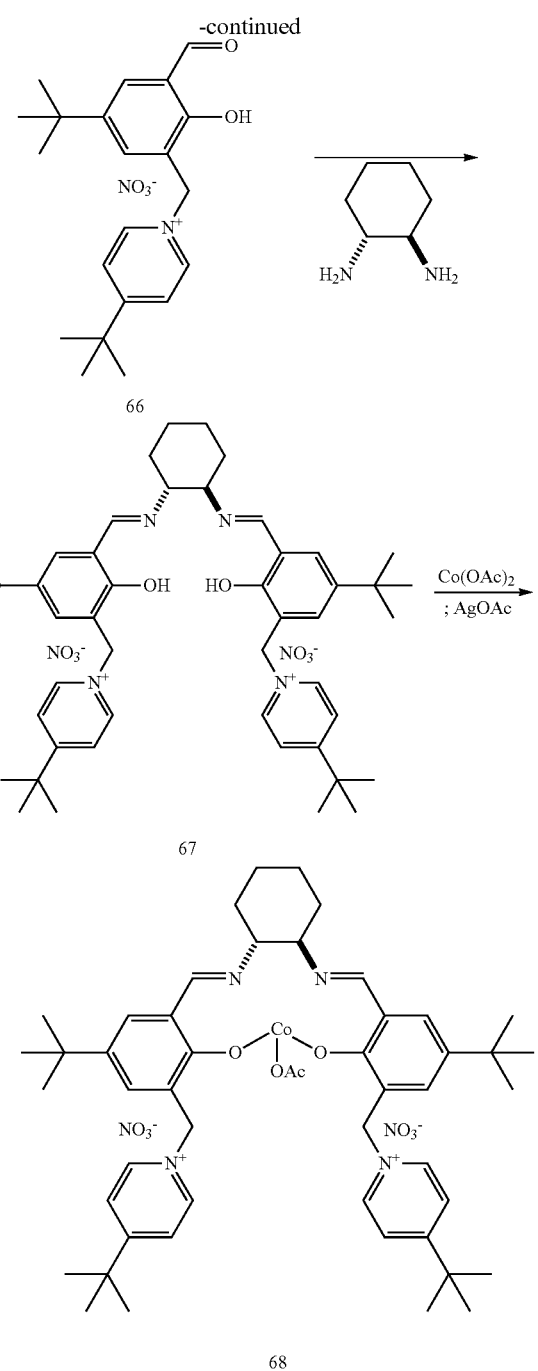

Bromomethyl salicylaldehyde 32 (1.0 g) prepared by the same method as Preparation Example 8 was dissolved in toluene (13 mL) and 4-tert-butyl pyridine (0.6 mL) was slowly put thereinto. The reactant was stirred at room temperature for 18 hours, diethyl ether (3 mL) was put thereinto, followed by additional stirring for 30 minutes. The obtained solid was filtered and washed with diethyl ether (10 mL) and then dried in vacuo. The reactant was dissolved in dichloromethane (11 mL) and silver nitrate (0.6 g) was put thereinto, followed by stirring at room temperature for 1 hour. The obtained solid was filtered and removed, followed by distillation under reduced pressure to obtain salicylaldehyde 66 containing ammonium salt (1.2 g). The obtained salicylaldehyde (1.2 g) was dissolved in ethanol (17 mL), and 1,2-trans-diaminocyclohexane (0.2 mL) was put thereinto, followed by stirring at room temperature for 12 hours. The reactant was distilled under reduced pressure to obtain a ligand 67 (1.3 g) containing ammonium salt. The prepared ligand (300 mg) was put into a round-bottom flask wrapped with aluminum foil and dissolved into dichloromethane (2 mL) under a nitrogen atmosphere, and cobalt acetate (62 mg) was put thereinto, followed by stirring at room temperature for 5 hours. After the reactant was exposed to air, silver acetate (68 mg) was put thereinto, followed by stirring at room temperature for 4 hours, a solid was removed by filtration and a solvent was removed by distillation under reduced pressure, thereby obtaining a symmetrical cobalt-salen catalyst 68 (341 mg) containing ammonium salt. Result obtained by spectroscopy experiment of the symmetrical salen ligand containing ammonium salt was as follows.

$^1$H-NMR (500 MHz, DMSO-$d_6$) δ 14.12 (2H, s), 8.98 (4H, d, J=7.0 Hz), 8.54 (2H, s), 8.46 (4H, d, J=7.0 Hz), 7.76 (2H, d, J=2.5 Hz), 7.40 (2H, d, J=2.5 Hz), 5.66 (4H, ABq, J=36.0, 13.5 Hz), 3.50 (2H, m), 1.87 (2H, m), 1.78 (2H, m), 1.58 (2H, m), 1.44 (2H, m), 1.32 (18H, s), 1.22 (18H, s)

Examples 1 to 5

Propylene oxide (PO) and each catalyst were put into a high pressure stainless steel reactor at each molar ratio as shown in the following Table 1 and the reactor was completely fastened. Carbon dioxide ($CO_2$) having ultra-high purity was slowly filled into the high pressure reactor and reaction was performed under predetermined pressure, operating temperature and time as shown in the following Table 1. After the reaction was completed, the reaction was cooled and remaining carbon dioxide was slowly discharged. After the catalyst was removed, the reactant was dried in vacuo to obtain poly(propylene carbonate). Physical properties of the obtained poly(propylene carbonate) were shown in the following Table 2.

TABLE 1

| Example | Catalyst | PO:Catalyst (Molar Ratio) | $CO_2$ Pressure (bar) | Reaction Temperature (° C.) | Reaction Time (hr) |
|---|---|---|---|---|---|
| 1 | Preparation Example 3 | 2,000:1 | 30 | 28 | 48 |

TABLE 1-continued

| Example | Catalyst | PO:Catalyst (Molar Ratio) | $CO_2$ Pressure (bar) | Reaction Temperature (° C.) | Reaction Time (hr) |
|---|---|---|---|---|---|
| 2 | Preparation Example 5 | 2,000:1 | 30 | 28 | 48 |
| 3 | Preparation Example 6 | 2,000:1 | 30 | 28 | 48 |
| 4 | Preparation Example 11 | 2,000:1 | 30 | 28 | 48 |
| 5 | Preparation Example 15 | 2,000:1 | 25 | 28 | 48 |

TABLE 2

| Example | PO Conversion Ratio | Selectivity | $M_n$ | PDI | TON |
|---|---|---|---|---|---|
| 1 | 82% | 99% | 7,600 | 1.22 | 1,624 |
| 2 | 63% | 99% | 7,400 | 1.21 | 1,247 |
| 3 | 63% | 99% | 4,100 | 1.26 | 1,247 |
| 4 | 48% | 99% | — | — | 950 |
| 5 | 13% | 80% | — | — | 208 |

Examples 6 to 19

Propylene oxide (PO), each catalyst and adipic acid were put into a high pressure stainless steel reactor at each molar ratio as shown in the following Table 3 and the reactor was completely fastened. A solvent was put thereinto as needed. Carbon dioxide ($CO_2$) having ultra-high purity was slowly filled into the high pressure reactor and reaction was performed under predetermined pressure, operating temperature and time as shown in the following Table 3. After the reaction was completed, the reaction was cooled and remaining carbon dioxide was slowly discharged. After the catalyst was removed, the reactant was dried in vacuo to obtain poly(propylene carbonate) and physical properties of the obtained poly(propylene carbonate) were shown in the following Table 4.

TABLE 3

| Example | Catalyst | PO:Catalyst: Adipic acid (Molar Ratio) | $CO_2$ Pressure (bar) | Reaction Temperature (° C.) | Reaction Time(hr) | Solvent | PO:Solvent(v/v) (Volume Ratio) |
|---|---|---|---|---|---|---|---|
| 6 | Preparation Example 1 | 10,000:1:500 | 30 | 40 | 53 | Toluene | 2:1 |
| 7 | Preparation Example 2 | 10,000:1:500 | 30 | 40 | 48 | Toluene | 2:1 |
| 8 | Preparation Example 3 | 2,000:1:100 | 30 | 28 | 48 | — | — |

TABLE 3-continued

| Example | Catalyst | PO:Catalyst:Adipic acid (Molar Ratio) | CO$_2$ Pressure (bar) | Reaction Temperature (° C.) | Reaction Time(hr) | Solvent | PO:Solvent(v/v) (Volume Ratio) |
|---|---|---|---|---|---|---|---|
| 9 | Preparation Example 4 | 2,000:1:10 | 30 | 28 | 48 | Toluene | 2:1 |
| 10 | Preparation Example 5 | 2,000:1:10 | 30 | 28 | 48 | — | — |
| 11 | Preparation Example 6 | 2,000:1:10 | 30 | 28 | 48 | — | — |
| 12 | Preparation Example 7 | 10,000:1:450 | 30 | 50 | 44 | Toluene | 2:1 |
| 13 | Preparation Example 8 | 2,000:1:10 | 30 | 25 | 48 | 1,2-dichloroethane | 2:1 |
| 14 | Preparation Example 8 | 2,000:1:100 | 30 | 50 | 48 | 1,2-dichloroethane | 3:2 |
| 15 | Preparation Example 9 | 2,000:1:100 | 30 | 50 | 66 | Toluene | 2:1 |
| 16 | Preparation Example 10 | 2,000:1:10 | 30 | 25 | 48 | — | — |
| 17 | Preparation Example 12 | 2,000:1:100 | 30 | 40 | 48 | 1,2-dichloroethane | 2:1 |
| 18 | Preparation Example 13 | 2,000:1:100 | 30 | 50 | 64 | Toluene | 2:1 |
| 19 | Preparation Example 14 | 2,000:1:100 | 30 | 50 | 64 | 1,2-dichloroethane | 2:1 |

TABLE 4

| Example | PO Conversion Ratio | Selectivity | M$_n$ | PDI | TON |
|---|---|---|---|---|---|
| 6 | 82% | 99% | 1,400 | — | 8,118 |
| 7 | 97% | 99% | 1,700 | — | 9,603 |
| 8 | 95% | 99% | 1,300 | 1.03 | 1,881 |
| 9 | 50% | 99% | 3,000 | 1.12 | 990 |
| 10 | 67% | 99% | 3,300 | 1.22 | 1,327 |
| 11 | 59% | 99% | 1,900 | 1.15 | 1,168 |
| 12 | 66% | 96% | 1,200 | — | 6,336 |
| 13 | 38% | 98% | — | — | 745 |
| 14 | 20% | 63% | — | — | 252 |
| 15 | 97% | 97% | — | — | 1,882 |
| 16 | 81% | 99% | 7,700 | 1.17 | 1,604 |
| 17 | 40% | 70% | — | — | 560 |
| 18 | 39% | 60% | — | — | 468 |
| 19 | 100% | 40% | — | — | 800 |

Comparative Examples 1 to 4

Propylene oxide (PO), each binary catalyst system of (Salen)Co compound (combination of the catalyst represented by the following Chemical Formula 23 and PPN$^+$Cl$^-$ represented by the following Chemical Formula 24), and adipic acid were put into a high pressure stainless steel reactor at each molar ratio as shown in the following Table 5 and the reactor was completely fastened. Carbon dioxide (CO$_2$) having ultra-high purity was slowly filled into the high pressure reactor and reaction was performed under predetermined pressure, operating temperature and time as shown in the following Table 5. After the reaction was completed, the reaction was cooled and remaining carbon dioxide was slowly discharged. After the catalyst was removed, the reactant was dried in vacuo to obtain poly (propylene carbonate) and physical properties of the obtained poly(propylene carbonate) were shown in the following Table 6.

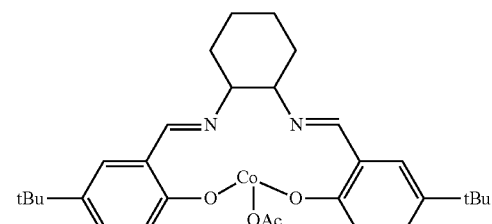

[Chemical Formula 23]

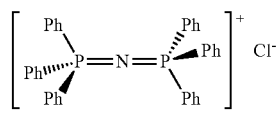

[Chemcial Formula 24]

PNCl, Bis(triphenylphosphine)iminium chloride

TABLE 5

| Comparative Example | Catalyst | PO:Chemical Formula 23:PPN$^+$Cl$^-$:Adipic acid (Molar Ratio) | CO$_2$ Pressure (bar) | Reaction Temperature (° C.) | Reaction Time (hr) |
|---|---|---|---|---|---|
| 1 | Chemical Formula 23 | 2,000:1:1:0 | 30 | 25 | 6 |
| 2 | Chemical Formula 23 | 2,000:1:1:10 | 30 | 25 | 5 |
| 3 | Chemical Formula 23 | 2,000:1:1:20 | 30 | 25 | 5 |

TABLE 5-continued

| Compara-tive Example | Catalyst | PO:Chemical Formula 23:PPN⁺Cl⁻:Adipic acid (Molar Ratio) | $CO_2$ Pressure (bar) | Reaction Temperature (° C.) | Reaction Time (hr) |
|---|---|---|---|---|---|
| 4 | Chemical Formula 23 | 2,000:1:1:30 | 30 | 25 | 5 |

TABLE 6

| Comparative Example | PO Conversion Ratio | Selectivity | $M_n$ | PDI |
|---|---|---|---|---|
| 1 | 93% | 96% | 9,174 | 1.369 |
| 2 | 91% | 100% | 7,973 | 1.156 |
| 3 | <5% | — | — | — |
| 4 | — | — | — | — |

Comparative Examples 1 to 4 above disclose preparation of poly(alkylene carbonate) by copolymerization of carbon dioxide/epoxide using a molecular weight regulator in the presence of the existing binary catalyst system of (Salen)Co compound. According to the appreciation from Tables 5 and 6, as relative equivalent of the molecular weight regulator with respect to the catalyst system is increased, activity of the catalyst system was deteriorated, for example, PO conversion ratio was decreased, and the like. In particular, it was appreciated that in which the relative equivalent of the molecular weight regulator is 20 or more, which is a general level, PO conversion ratio was rapidly decreased to be less than 5%, such that it was determined that activity of the catalyst system was not effectively maintained. Therefore, there is a limitation in obtaining low molecular weight of copolymer at desirable level by adding the molecular weight regulator at a general quantitative level in the presence of the existing binary catalyst system.

However, according to the preparation method of the present invention disclosed in Examples of Tables 1 to 4, it was appreciated that in the case in which the relative equivalent of the molecular weight regulator as compared to the catalyst system was 20 to 500 which is a general level, PO conversion ratio was obtained as an appropriate value. In particular, it was appreciated that even though the relative equivalent of the molecular weight regulator adopted 10 to 500 which was a broad range, low molecular weight of copolymer at an appropriate level was stably provided without a remarkable decrease in activity of the catalyst.

In addition, it was appreciated that according to Examples of Tables 1 to 4, the catalyst of the present invention effectively promoted the reaction even under a relatively low copolymerization temperature condition which was 20° C. to 50° C.

The invention claimed is:

1. A complex represented by the following Chemical Formula 1:

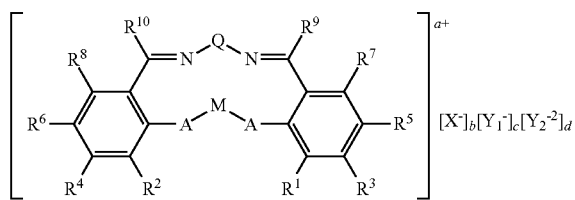

[Chemical Formula 1]

wherein
M is trivalent cobalt or trivalent chromium;
A is an oxygen or sulfur atom;
Q is a diradical that connects two nitrogen atoms;
X⁻ is a halogen anion; a (C6-C20)aryloxy anion; a (C6-C20)aryloxy anion containing one or more selected from among a halogen atom, a nitrogen atom, an oxygen atom, a silicon atom, a sulfur atom and a phosphorus atom; a (C1-C20)alkylcarboxyl anion; a (C1-C20)alkylcarboxyl anion containing one or more selected from among a halogen atom, a nitrogen atom, an oxygen atom, a silicon atom, a sulfur atom and a phosphorus atom; a (C6-C20)arylcarboxyl anion; a (C6-C20)arylcarboxyl anion containing one or more selected from among a halogen atom, a nitrogen atom, an oxygen atom, a silicon atom, a sulfur atom and a phosphorus atom; a (C1-C20)alkoxy anion; a (C1-C20)alkoxy anion containing one or more selected from among a halogen atom, a nitrogen atom, an oxygen atom, a silicon atom, a sulfur atom and a phosphorus atom; a (C1-C20)alkylcarbonate anion; a (C1-C20)alkylcarbonate anion containing one or more selected from among a halogen atom, a nitrogen atom, an oxygen atom, a silicon atom, a sulfur atom and a phosphorus atom; a (C6-C20)arylcarbonate anion; a (C6-C20)arylcarbonate anion containing one or more selected from among a halogen atom, a nitrogen atom, an oxygen atom, a silicon atom, a sulfur atom and a phosphorus atom; a (C1-C20)alkylsulfonate anion; a (C1-C20)alkylsulfonate anion containing one or more selected from among a halogen atom, a nitrogen atom, an oxygen atom, a silicon atom, a sulfur atom and a phosphorus atom; a (C1-C20)alkylamido anion; a (C1-C20)alkylamido anion containing one or more selected from among a halogen atom, a nitrogen atom, an oxygen atom, a silicon atom, a sulfur atom and a phosphorus atom; a (C6-C20)arylamido anion; a (C6-C20)arylamido anion containing one or more selected from among a halogen atom, a nitrogen atom, an oxygen atom, a silicon atom, a sulfur atom and a phosphorus atom; a (C1-C20)alkylcarbamate anion; a (C1-C20)alkylcarbamate anion containing one or more selected from among a halogen atom, a nitrogen atom, an oxygen atom, a silicon atom, a sulfur atom and a phosphorus atom; a (C6-C20)arylcarbamate anion; or a (C6-C20)arylcarbamate anion containing one or more selected from among a halogen atom, a nitrogen atom, an oxygen atom, a silicon atom, a sulfur atom and a phosphorus atom;
$Y_1^-$ is F⁻, Cl⁻, Br⁻, I⁻, $BF_4^-$, $ClO_4^-$, $NO_3^-$ or $PF_6^-$;
$Y_2^{-2}$ is $SO_4^{-2}$ or $CO_3^{-2}$;
a is an integer obtained by adding 1 to the total number of monovalent cations included in protonated groups of $R^1$ to $R^{10}$;

b is an integer of 1 or more, c is an integer of 0 or more, d is an integer of 0 or more, and b+c+2d=a is satisfied;

$R^1$ to $R^{10}$ are each independently hydrogen; halogen; (C1-C20)alkyl; (C1-C20)alkyl containing one or more selected from the group consisting of halogen, nitrogen, oxygen, silicon, sulfur and phosphorus; (C2-C20)alkenyl; (C2-C20)alkenyl containing one or more selected from the group consisting of halogen, nitrogen, oxygen, silicon, sulfur and phosphorus; (C1-C20)alkyl(C6-C20)aryl; (C1-C20)alkyl(C6-C20)aryl containing one or more selected from the group consisting of halogen, nitrogen, oxygen, silicon, sulfur and phosphorus; (C6-C20)aryl(C1-C20)alkyl; (C6-C20)aryl(C1-C20)alkyl containing one or more selected from the group consisting of halogen, nitrogen, oxygen, silicon, sulfur and phosphorus; (C1-C20)alkoxy; (C6-C30)aryloxy; formyl; (C1-C20)alkylcarbonyl; (C6-C20)arylcarbonyl; a metalloid radical of Group 14 metal substituted with hydrocarbyl; a protonated group of the following Chemical Formula 2; a protonated group of the following Chemical Formula 3; a protonated group of the following Chemical Formula 5; a protonated group of the following Chemical Formula 6; or a protonated group of the following Chemical Formula 7;

wherein at least two or more of $R^1$ to $R^{10}$ are a protonated group selected from a group consisting of the following Chemical Formulas 2, 3, 5, 6 and 7;

[Chemical Formula 2]

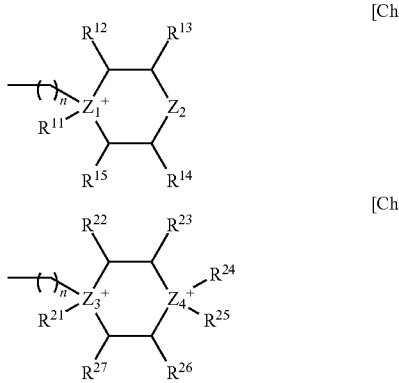

[Chemical Formula 3]

$Z_1, Z_3, Z_4, Z_6, Z_7, Z_8, Z_9, Z_{11}$ and $Z_{12}$ are each independently an nitrogen atom or a phosphorus atom;

$Z_2$ and $Z_{10}$ are each independently an oxygen atom, a sulfur atom or a methylene group (—$CH_2$—);

n is an integer of 1 to 10;
m is an integer of 1 to 10;
$R^{11}, R^{12}, R^{13}, R^{14}, R^{15}, R^{21}, R^{22}, R^{23}, R^{24}, R^{25}, R^{26}, R^{27}, R^{41}, R^{42}, R^{43}, R^{44}, R^{45}, R^{51}, R^{52}, R^{53}, R^{54}, R^{55}, R^{61}, R^{62}, R^{63}, R^{64}, R^{65}, R^{66}, R^{67}, R^{71}, R^{72}, R^{73}$ and $R^{74}$ are each independently hydrogen; (C1-C20)alkyl; (C1-C20)alkyl containing one or more selected from the group consisting of halogen, nitrogen, oxygen, silicon, sulfur and phosphorus; (C2-C20)alkenyl; (C2-C20)alkenyl containing one or more selected from the group consisting of halogen, nitrogen, oxygen, silicon, sulfur and phosphorus; (C1-C20)alkyl(C6-C20)aryl; (C1-C20)alkyl(C6-C20)aryl containing one or more selected from the group consisting of halogen, nitrogen, oxygen, silicon, sulfur and phosphorus; (C6-C20)aryl (C1-C20)alkyl; (C6-C20)aryl(C1-C20)alkyl containing one or more selected from the group consisting of halogen, nitrogen, oxygen, silicon, sulfur and phosphorus; or a metalloid radical of Group 14 metal substituted with hydrocarbyl.

2. The complex of claim 1, wherein Q is (C6~C30)arylene, (C1~C20)alkylene, (C2~C20)alkenylene, (C2~C20)alkynylene or (C3~C20)cycloalkylene.

3. The complex of claim 2, wherein M is trivalent cobalt; A is oxygen; and Q is 1,2-cyclohexylene, phenylene or ethylene.

4. The complex of claim 1, wherein at least two or more of $R^1, R^2, R^5$ and $R^6$ are a protonated group selected from the group consisting of Chemical Formulas 2, 3, 5, 6 and 7 of claim 1; or two of $R^1, R^2, R^5$ and $R^6$ are linked with each other by a protonated group of Chemical Formula 8 to thereby form a ring.

5. The complex of claim 4, wherein $R^3, R^4, R^7, R^8, R^9$ and $R^{10}$ are each hydrogen.

6. The complex of claim 1, wherein $X^-$ is coordinated to M.

7. The complex of claim 1, wherein two of $R^1$ to $R^{10}$ are linked with each other by a protonated group of Chemical Formula 8 to thereby form a ring.

8. The complex of claim 1, wherein two of $R^{11}, R^{12}, R^{13}, R^{14}$ and $R^{15}$, two of $R^{21}, R^{22}, R^{23}, R^{24}, R^{25}, R^{26}$ and $R^{27}$, two of $R^{41}, R^{42}, R^{43}, R^{44}$ and $R^{45}$, two of $R^{51}, R^{52}, R^{53}, R^{54}$ and $R^{55}$, two of $R^{61}, R^{62}, R^{63}, R^{64}, R^{65}, R^{66}$ and $R^{67}$ or two of $R^{71}, R^{72}, R^{73}$ and $R^{74}$ are linked with each other to thereby form a ring.

9. The complex of claim 1, wherein two of $R^1$ to $R^{10}$ are linked with each other by a protonated group of Chemical Formula 8 to thereby form a ring.

* * * * *

UNITED STATES PATENT AND TRADEMARK OFFICE
CERTIFICATE OF CORRECTION

PATENT NO. : 9,969,842 B2  
APPLICATION NO. : 14/777861  
DATED : May 15, 2018  
INVENTOR(S) : Jong Chan Kim et al.

Page 1 of 2

It is certified that error appears in the above-identified patent and that said Letters Patent is hereby corrected as shown below:

In the Claims

Column 57, Line 27, Claim 1, delete "6 and 7;" and insert -- 6, 7 and 8; --

Column 57, Line 45, Claim 1, after

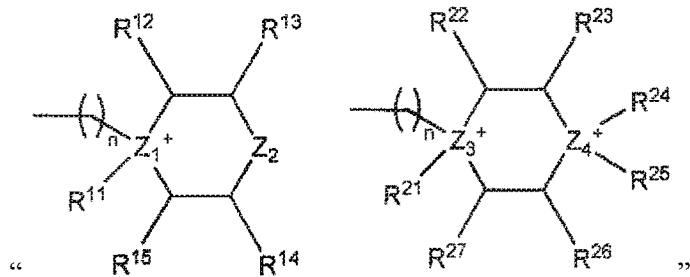

Signed and Sealed this  
Thirteenth Day of November, 2018

Andrei Iancu  
*Director of the United States Patent and Trademark Office*

CERTIFICATE OF CORRECTION (continued)
U.S. Pat. No. 9,969,842 B2

[Chemical Formula 5]

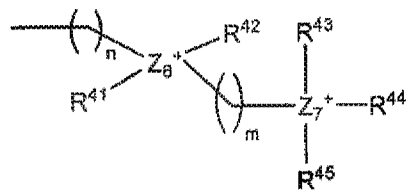

[Chemical Formula 6]     [Chemical Formula 7]

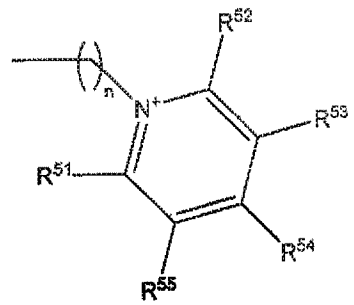 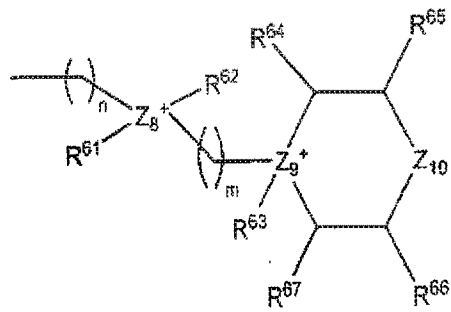

[Chemical Formula 8]

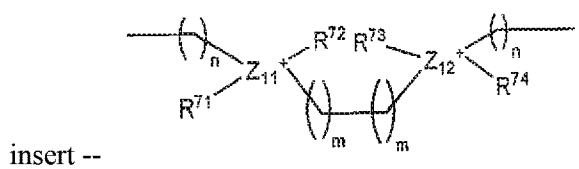

insert -- --

Column 58, Line 2, Claim 1, after "10;" insert -- and --